(12) United States Patent
Strongin et al.

(10) Patent No.: US 8,927,727 B2
(45) Date of Patent: Jan. 6, 2015

(54) THIOL DETECTION

(75) Inventors: Robert Michael Strongin, Portland, OR (US); Martha Sibrian-Vazquez, Portland, OR (US)

(73) Assignee: The State of Oregon Acting by and through the State Board of Higher Education on behalf of Portland State University, Portland, OR (US)

( * ) Notice: Subject to any disclaimer, the term of this patent is extended or adjusted under 35 U.S.C. 154(b) by 0 days.

(21) Appl. No.: 13/539,191

(22) Filed: Jun. 29, 2012

(65) Prior Publication Data

US 2012/0276649 A1 Nov. 1, 2012

Related U.S. Application Data

(63) Continuation-in-part of application No. PCT/US2010/062582, filed on Dec. 30, 2010.

(60) Provisional application No. 61/335,101, filed on Dec. 30, 2009.

(51) Int. Cl.

| | | |
|---|---|---|
| *C07D 213/26* | (2006.01) | |
| *C07D 401/14* | (2006.01) | |
| *C07D 213/22* | (2006.01) | |
| *C07D 401/04* | (2006.01) | |
| *C07D 405/14* | (2006.01) | |
| *C07D 493/10* | (2006.01) | |
| *G01N 31/22* | (2006.01) | |

(52) U.S. Cl.
CPC ............ *C07D 401/14* (2013.01); *C07D 213/22* (2013.01); *C07D 401/04* (2013.01); *C07D 405/14* (2013.01); *C07D 493/10* (2013.01); *G01N 31/22* (2013.01)
USPC ....................................................... 546/258

(58) Field of Classification Search
None
See application file for complete search history.

(56) References Cited

U.S. PATENT DOCUMENTS

| | | | |
|---|---|---|---|
| 4,769,467 | A | 9/1988 | Imai |
| 5,130,433 | A | 7/1992 | Albarella et al. |
| 5,227,487 | A | 7/1993 | Haugland et al. |
| 6,534,316 | B2 | 3/2003 | Strongin et al. |
| 2003/0206326 | A1 | 11/2003 | Berneth et al. |
| 2008/0261315 | A1 | 10/2008 | Strongin et al. |
| 2009/0311142 | A1 | 12/2009 | Burgess-Cassler et al. |
| 2010/0051826 | A1 | 3/2010 | Strongin et al. |
| 2010/0273763 | A1 | 10/2010 | Brard et al. |

FOREIGN PATENT DOCUMENTS

| | | |
|---|---|---|
| WO | WO 01/88060 | 11/2001 |
| WO | WO 2005/110109 | 11/2005 |
| WO | WO 2008/011508 | 1/2008 |
| WO | WO 2009/152513 | 12/2009 |

OTHER PUBLICATIONS

Caplus 1982:605815.*
Caplus 1987:439063.*
International Search Report and Written Opinion dated Oct. 20, 2011, from related International Application No. PCT/US2010/062582.
Shao et al., "Design of Bis-spiropyran Ligands as Dipolar Molecule Receptors and Application to in Vivo Glutathione Fluorescent Probes," *Journal of the American Chemical Society* 30:20, p. A-L (2009).
Yang et al., "A Convenient Preparation of Xanthene Dyes," *Journal of Organic Chemistry* 70:17, p. 6907-6912 (Jul. 2005).
Yang et al., "An Organic White Light-Emitting Fluorophore," *Journal of the American Chemical Society* 128:43, p. 14081-14092 (Oct. 2006).
Yang et al., "An Organic White Light-Emitting Fluorophore," *Journal of the American Chemical Society* 129, p. 1008 (Jan. 2007).
Yang et al., "Seminaphthofluorones are a family of water-soluble, low molecular weight, NIR-emitting fluorophores," *PNAS* 105:26, p. 8829-8834 (Jul. 2008).
Extended European Search Report for related European Application No. 10841755.1, dated Nov. 21, 2013, 12 pages.
Schrauzer et al., "Electron Transfer Reactions Catalyzed by Vitamin $B_{12}$ and Related Compounds: The Reduction of Dyes and of Riboflavin by Thiols," *Archives of Biochemistry and Biophysics* 130:257-266, 1969.
Sibrian-Vazquez et al., "Homocystamides promote free-radical and oxidative damage to proteins," *PNAS* 107(2):551-554, Jan. 12, 2010.
First Office Action, dated Jan. 27, 2014, issued in corresponding China Patent Application No. 201080065019.4.
Search Report, dated Jan. 21, 2014, issued in corresponding China Patent Application No. 201080065019.4, 2 pages.
Sharrett, et al., "Boronic Acid-Appended Bis-Viologens as a New Family of Viologen Quenchers for Glucose Sensing," *Tetrahedron Letters* (2008), vol. 49, pp. 300-304.
Geuder, et al., "Single and Double Bridged Viologenes and Intramolecular Pimerization of their Cation Radicals," *Tetrahedron*, (1986), vol. 42, No. 6, pp. 1665-1677.
Yamaguchi, et al., "Electrochemical Characteristics of Viologen Carboxylic Acid Derivatives Assembled onto Au Electrode as a Synthetic Receptor for Electron-Rich Compounds," *Electrochimica Acta*, (2001), vol. 46, No. 16, pp. 2527-2535.

* cited by examiner

*Primary Examiner* — Heidi Reese
(74) *Attorney, Agent, or Firm* — Klarquist Sparkman, LLP

(57) ABSTRACT

Embodiments of compounds for selectively detecting a thiol are disclosed. In some embodiments, the compounds are bridged viologens, and the compounds are capable of reacting with homocysteine and/or glutathione in a buffered solution to produce a change in the solution's absorbance spectrum and/or emission spectrum. Also disclosed are embodiments of methods and kits for detecting homocysteine and/or glutathione with the disclosed bridged viologens.

17 Claims, 24 Drawing Sheets
(20 of 24 Drawing Sheet(s) Filed in Color)

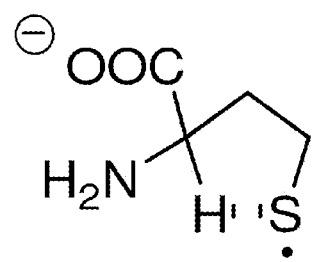
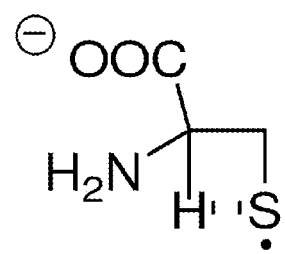
FIG. 1A  FIG. 1B
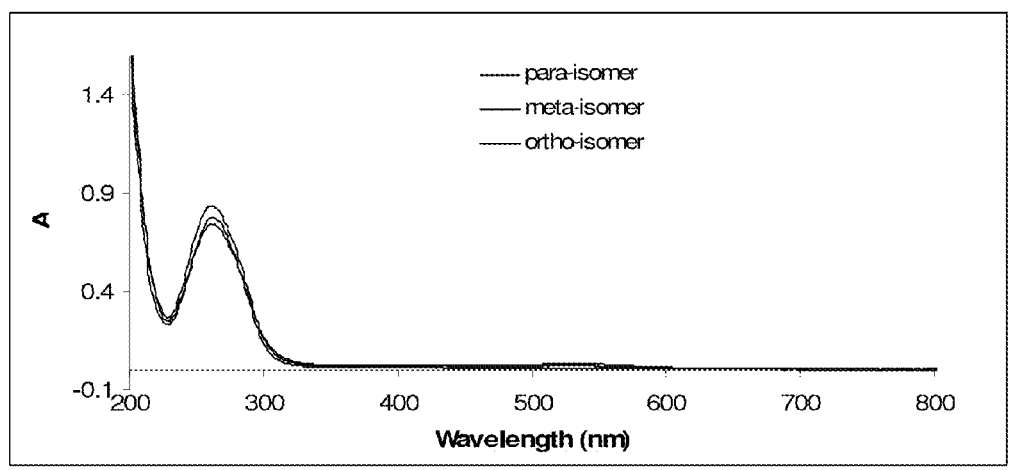
FIG. 2

1 minute, RT           30 minutes, RT 1 minute, RT           30 minutes, RT 1 minute, RT          30 minutes, RT 1 minute, RT          30 minutes, RT 1 minute, RT        30 minutes, RT 10 minutes, RT 1 minute, reflux / 5 minutes, reflux 1 minute, reflux      5 minutes, reflux ortho-

THIOL DETECTION

CROSS REFERENCE TO RELATED APPLICATIONS

This is a continuation-in-part of International Application No. PCT/US2010/062582, filed Dec. 30, 2010, which claims the benefit of U.S. Provisional Patent Application No. 61/335,101, filed Dec. 30, 2009, each of which is incorporated herein by reference in its entirety.

ACKNOWLEDGMENT OF GOVERNMENT SUPPORT

This invention was made with government support under grant R01 EB002044 awarded by the National Institutes of Health. The government has certain rights in the invention.

FIELD

Embodiments of compounds, methods, and kits for the determination of thiols, such as glutathione or both glutathione and homocysteine, are disclosed.

BACKGROUND

The detection of biologically important thiols has been the focus of much research. Different naturally-occurring thiols, which may have similar structures, may have quite different physiological properties. The physiological effects and correlations that have been observed for these thiols are a public health concern. Examples of low molecular weight thiols that have more-or-less similar structures, but that have disparate physiological properties, include cysteine (Cys), homocysteine (Hcy), glutathione (GSH), N-acetylcysteine, and penicillamine.

Glutathione is of particular interest to medical researchers. Glutathione levels are indicative of oxidative stress. Additionally, low glutathione levels may be linked, for example, to mitochondrial diseases, autism, and mercury poisoning.

Thiols are easily oxidized, and are typically colorless and non-fluorescent at visible wavelengths. Most reported methods for thiol detection have been based upon nonspecific redox chemistry, immunoassays, or upon derivatization with chromophores or fluorophores. Generic methods for detecting thiols do not readily distinguish among the structurally similar species. There is a substantial need for improved methods for detecting and quantifying biological thiols.

Methylviologen ($MV^{2+}$) is a 4,4'-dipyridyl dication:

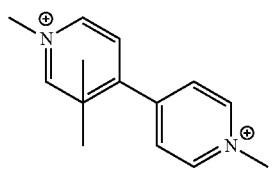

$MV^{2+}$ has been used as an oxidant in an investigation of the equilibrium kinetics of both the reducing disulfide and the α-amino carbon-centered radicals derived from Hcy, Cys and GSH. Reducing radical formation was monitored via changes in the UV-Vis spectra of solutions containing the methylviologen radical cation that formed in the presence of the biological thiols. See R. Zhao et al., "Kinetics of one-electron oxidation of thiols and hydrogen abstraction by thiyl radicals from α-amino C—H bonds," *J. Am. Chem. Soc.*, vol. 116, pp. 12010-12015 (1994); and R. Zhao et al., "Significance of the intramolecular transformation of glutathione thiyl radicals to α-aminoalkyl radicals. Thermochemical and biological implications," *J. Chem. Soc., Perkins Trans.*, vol. 2, pp. 569-574 (1997) It was surmised that formation of the reducing α-aminoalkyl radical derived from Hcy should be particularly favorable, due to an intramolecular hydrogen abstraction mechanism involving a five-atom ring transition state (See FIG. 1A). By contrast, in the case of either Cys or GSH, H-atom abstraction to a reducing carbon-centered radical would proceed via less-favored four-membered ring (FIG. 1B) or nine-membered ring (not shown) transition state geometries, respectively. See FIGS. 1A and 1B, depicting the inferred proton abstraction leading to formation of the α-aminoalkyl radical from the thiyl radicals of Hcy and Cys, respectively. These references do not disclose any appreciable colorimetric selectivity among homocysteine, cysteine, and glutathione.

U.S. Publication 2008/0261315, which is incorporated herein by reference, discloses a method for selectively determining homocysteine with methylviologen. Heating a sample containing Hcy with a colorless solution of methylviologen for five minutes or longer at a temperature between about 25° C. and 1 10° C. and a pH between about 3.9 and about 9.5 produces a visible color change. Color formation can be monitored via the appearance of absorption peaks at 398 nm and 605 nm. In contrast, samples containing Cys or GSH remain colorless when heated with a solution of methylviologen under similar conditions.

SUMMARY

Embodiments of compounds for selectively detecting cysteine, homocysteine, and/or glutathione are disclosed. Also disclosed are embodiments of methods and kits for performing the detection.

Embodiments of the disclosed compounds when reacted with one or more thiols in solution, particularly cysteine, homocysteine, glutathione, or combinations thereof, produce a detectable change in the solution's absorbance spectrum and/or emission spectrum. Disclosed embodiments of the compounds are bridged viologens with a structure according to Formula I, II, or III:

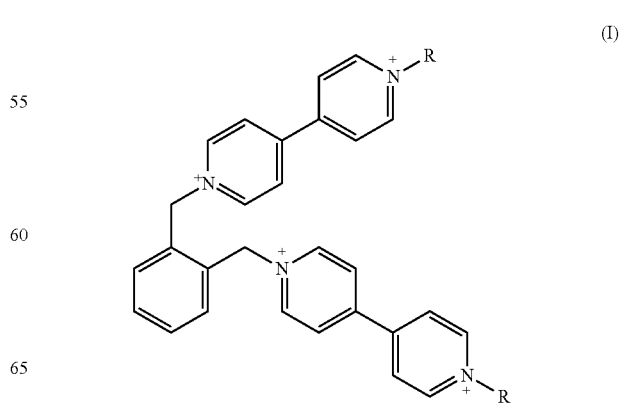

-continued

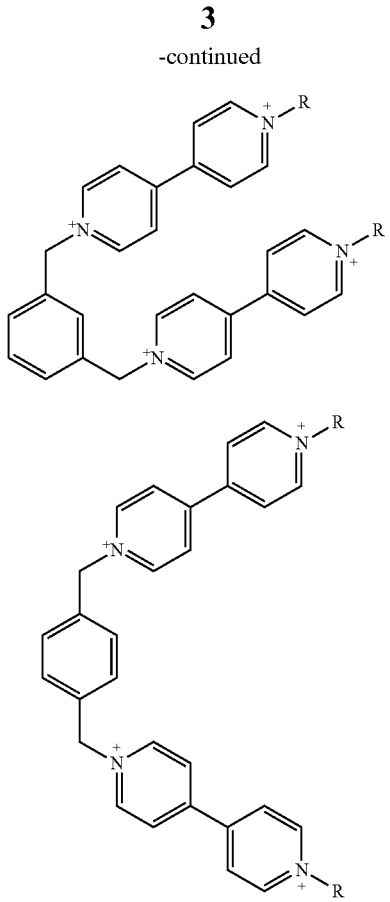

where R is a lower alkyl nitrile, lower alkyl-substituted phenyl, alkenyl, alkynyl, substituted coumarin, acetal, carboxylate group, or a fluorophore. In some embodiments, the fluorophore is a compound according to the formula

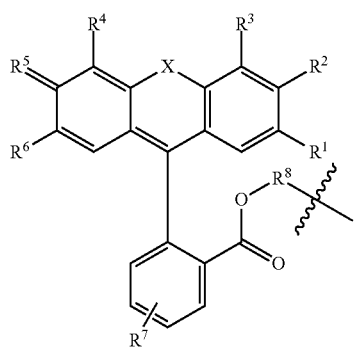

where X is oxygen, sulfur, $CH_2$ or NH; $R^1$, $R^2$, $R^3$, $R^4$, and $R^6$ independently are selected from —H, —OH, lower alkyl, carboxyalkyl, amino, substituted amino, alkoxy, or halogen, or $R^2$ and $R^3$ together may form a substituted or unsubstituted cycloalkyl or aryl; $R^5$ is oxygen, imino, substituted alkyl imino, or substituted or unsubstituted cycloalkyl imino; $R^7$ is —H, alkyl, acyl, carboxyl, nitro, amino, substituted amino; and $R^8$ is absent or alkyl.

In some embodiments, R is cyanomethyl, benzyl, allyl, propargyl, 1-(2-oxo-2-2H-chromen-3-yl)ethyl, 1-(2,2-dihydroxyethyl), 1-carboxymethyl, or 3-(2-(10-(dimethylimino)-1-hydroxy-10H-benzo[c]xanthen-7-yl)benzoyloxy)propyl.

In particular embodiments, the compound is 1',1"-(1,4-phenylenebis(methylene))bis(1-(cyanomethyl)-4,4'-bipyridine-1,1'-diium)bromide, 1',1"-(1,3-phenylenebis(methylene))bis(1-(cyanomethyl)-4,4'-bipyridine-1,1'-diium)bromide, 1',1"-(1,2-phenylenebis(methylene))bis(1-(cyanomethyl)-4,4'-bipyridine-1,1'-diium)bromide, 1',1"-(1,4-phenylenebis(methylene))bis(1-(benzyl)-4,4'-bipyridine-1,1'-diium)bromide, 1',1"-(1,4-phenylenebis(methylene))bis(1-allyl-4,4'-bipyridine-1,1'-diium)bromide, 1',1"-(1,4-phenylenebis(methylene))bis(1-propargyl-1-4,4'-bipyridine-1,1'-diium)bromide, 1',1"-(1,4-phenylenebis(methylene))bis(1-(2-oxo-2-(2-oxo-2H-chromen-3-yl)ethyl)-4,4'-bipyridine-1,1'-diium)bromide, 1',1"-(1,4-phenylenebis(methylene))bis(1-(2,2-dihydroxyethyl)-4,4'-bipyridine-1,1'-diium)bromide, 1',1"-(1,4-phenylenebis(methylene))bis(1-(carboxymethyl)-4,4'-bipyridine-1,1'-diium)bromide, or mono(1',1"-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide.

Also disclosed are embodiments of methods for detecting a thiol. A solution is formed by combining a sample comprising a thiol (e.g., cysteine, homocysteine, glutathione, or a combination thereof) with a compound having Formula I, II, or III, where R is as previously recited. A reaction between the thiol and the compound is allowed to proceed in solution for an effective period of time to produce a detectable change in the solution's absorbance spectrum and/or emission spectrum, where the change indicates that the thiol is present. The change is then detected qualitatively, such as by a visual color comparison or a change in the absorbance spectrum and/or emission spectrum, or quantitatively, such as by monitoring a change in absorbance and/or emission of the solution at one or more wavelengths as a function of time. In certain embodiments, the solution further comprises a buffer selected from HEPES (N'-2-hydroxyethylpiperazine-N'-2-ethanesulfonic acid), MOPS (3-(N-morpholino)propanesulfonic acid), phosphate, and TRIS (tris(hydroxymethyl)-aminomethane) buffers. In some embodiments, the reaction proceeds at room temperature for 1-60 minutes, or 1-30 minutes. In other embodiments, the reaction proceeds under reflux conditions for 1-5 minutes. In particular embodiments, the thiol is homocysteine, glutathione, or a combination thereof, the buffer is a phosphate or TRIS buffer, and the compound is 1',1"-(1,4-phenylenebis(methylene))bis(1-(cyanomethyl)-4,4'-bipyridine-1,1'-diium)bromide, 1',1"-(1,3-phenylenebis(methylene))bis(1-(cyanomethyl)-4,4'-bipyridine-1,1'-diium)bromide, 1',1"-(1,4-phenylenebis(methylene))bis(1-(benzyl)-4,4'-bipyridine-1,1'-diium)bromide, and 1',1"-(1,4-phenylenebis(methylene))bis(1-allyl-4,4'-bipyridine-1,1'-diium)bromide, or a combination thereof.

Embodiments of kits for detecting a thiol are disclosed. In some embodiments, the kits include at least one compound suitable for selectively detecting a thiol (e.g., cysteine, homocysteine, glutathione, or a combination thereof), and a buffer in which the compound when combined with the thiol has an absorbance spectrum, an emission spectrum, or both that differs from an absorbance spectrum, an emission spectrum, or both when the thiol is absent.

The compound has Formula I, II, or III, where R is as previously recited. In some embodiments, the compound is selected from 1',1"-(1,4-phenylenebis(methylene))bis(1-(cyanomethyl)-4,4'-bipyridine-1,1'-diium)bromide, 1',1"-(1,3-phenylenebis(methylene))bis(1-(cyanomethyl)-4,4'-bipyridine-1,1'-diium)bromide, 1',1"-(1,2-phenylenebis(methylene))bis(1-(cyanomethyl)-4,4'-bipyridine-1,1'-diium)bromide, 1',1"-(1,4-phenylenebis(methylene))bis(1-(benzyl)-4,4'-bipyridine-1,1'-diium)bromide, 1',1"-(1,4-phenylenebis(methylene))bis(1-allyl-4,4'-bipyridine-1,1'- diium)bromide, 1',1"-(1,4-phenylenebis(methylene))bis(1-propargyl-4,4'-bipyridine-1,1'-diium)bromide, 1',1"-(1,4-phenylenebis(methylene))bis(1-(2-oxo-2-(2-oxo-2H-chromen-3-yl)ethyl)-4,4'-bipyridine-1,1'-diium)bromide, 1',1"-(1,4-phenylenebis(methylene))bis(1-(2,2-dihydroxy-ethyl)-4,4'-bipyridine-1,1'-diium)bromide, 1',1"-(1,4-phenylenebis(methylene))bis(1-(carboxymethyl)-4,4'-bipyridine-1,1'-diium)bromide, mono(1',1"-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide, or a combination thereof. In certain embodiments, the compound is selected from 1',1"-(1,4-phenylenebis(methylene))bis(1-(cyanomethyl)-4,4'-bipyridine-1,1'-diium)bromide, 1',1"-(1,3-phenylenebis(methylene))bis(1-(cyanomethyl)-4,4'-bipyridine-1,1'-diium)bromide, 1',1"-(1,4-phenylenebis(methylene))bis(1-(benzyl)-4,4'-bipyridine-1,1'-diium)bromide, 1',1"-(1,4-phenylenebis(methylene))bis(1-allyl-4,4'-bipyridine-1,1'-diium)bromide, 1',1"-(1,4-phenylenebis(methylene))bis(1-(2-oxo-2-(2-oxo-2H-chromen-3-yl)ethyl)-4,4'-bipyridine-1,1'-diium)bromide, mono(1',1"-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide, or a combination thereof. In some embodiments, the buffer is a HEPES (N'-2-hydroxyethylpiperazine-N'-2-ethanesulfonic acid), MOPS (3-(N-morpholino)propanesulfonic acid), phosphate, or TRIS (tris(hydroxymethyl)-aminomethane) buffer.

In some embodiments, the kit further includes a color comparison chart for evaluating a color change produced by a reaction between (a) the compound and (b) cysteine, homocysteine, glutathione, or a combination thereof. In some embodiments, the kit also includes a plurality of disposable containers in which a reaction between the compound and a thiol can be performed. In particular embodiments, an amount of the compound effective to undergo a detectable change in the absorbance spectrum, the emission spectrum, or both when reacted with a thiol is premeasured into the plurality of disposable containers.

The foregoing and other objects, features, and advantages of the invention will become more apparent from the following detailed description, which proceeds with reference to the accompanying figures, at least some of which are submitted in full color.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B depict the inferred proton abstraction leading to formation of an α-aminoalkyl radical from the thiyl radicals of homocysteine and cysteine, respectively.

FIG. 2 is the UV-vis absorbance spectra of the ortho-, meta-, and para-isomers of bridged bis-CN viologens.

DETAILED DESCRIPTION

I. Terms and Definitions

Figure 3:
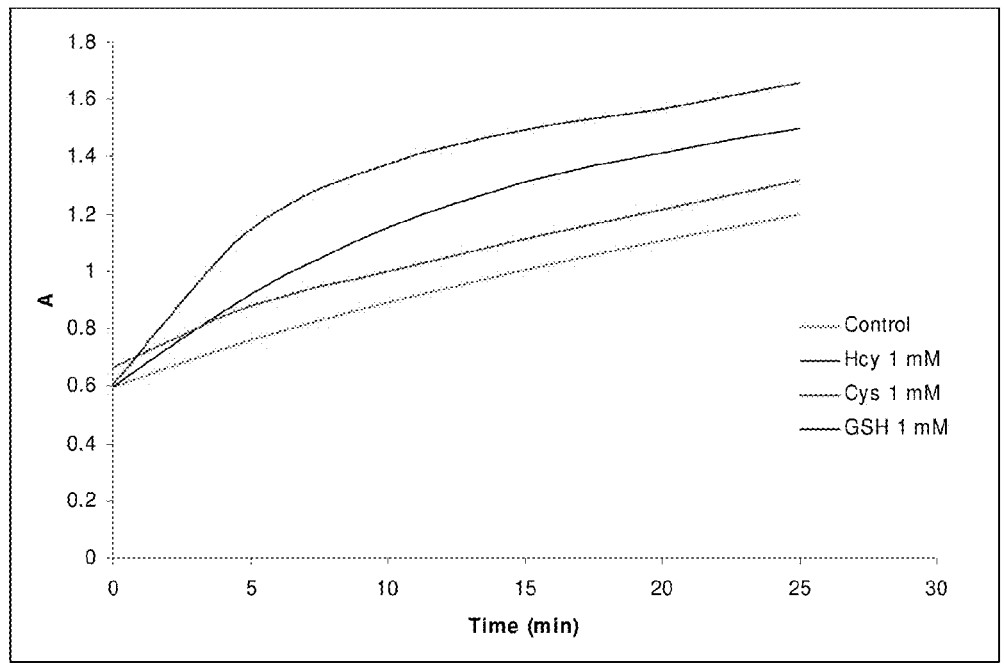
FIG. 3 is a graph of absorbance at 534 nm versus time for the reaction of ortho-bridged bis-CN viologen with thiols.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Absorbance: The retention by a compound or substance of certain wavelengths of radiation incident upon it; a measure of the amount of light at a particular wavelength absorbed as the light passes through a compound or substance, or through a solution of a compound or substance.

The term aliphatic means having a branched or unbranched carbon chain. The chain may be saturated (having all single bonds) or unsaturated (having one or more double or triple bonds).

Alkyl refers to a hydrocarbon group having a saturated carbon chain. The chain may be branched or unbranched. The term lower alkyl means the chain includes 1-10 carbon atoms.

An analogue or derivative is a compound that is derived from a similar compound, or a compound that can be imagined to arise from another compound, for example, if one atom is replaced with another atom or group of atoms. Analogues may differ from one another inone or more atoms, functional groups, or substructures, which are replaced with other atoms, groups, or substructures.

Aromatic or aryl compounds typically are unsaturated, cyclic hydrocarbons having alternate single and double bonds. Benzene, a 6-carbon ring containing three double bonds, is a typical aromatic compound.

Detect: To determine if an agent (such as a target molecule) is present or absent, for example, in a sample. "Detecting" refers to any method of determining if something exists, or does not exist, such as determining if a target molecule is present in a biological sample. For example, "detecting" can include using a visual or a mechanical device to determine if a sample displays a specific characteristic.

Emission or emission signal: The light of a particular wavelength generated from a source. In particular examples, an emission signal is emitted from a fluorophore after the fluorophore absorbs light at its excitation wavelength(s).

Fluorescence is the emission of visible radiation by an atom or molecule passing from a higher to a lower electronic state, wherein the time interval between absorption and emission of energy is $10^{-8}$ to $10^{-3}$ second. Fluorescence occurs when the atom or molecule absorbs energy from an excitation source (e.g., an ultraviolet lamp) and then emits the energy as visible radiation.

A fluorophore, or fluorogen, is a compound capable of fluorescence, such as a fluorescent dye. The term "fluorophore" also refers to the portion of a molecule that causes the molecule to fluoresce when exposed to an excitation source.

A functional group is a specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulthydryl), disulfide.

Heteroaryl compounds are aromatic compounds having at least one heteroatom, i.e., one or more carbon atoms in the ring has been replaced with an atom having at least one lone pair of electrons, typically nitrogen, oxygen, or sulfur.

A rhodol is a structural hybrid of fluorescein and a rhodamine. Rhodamines are a family of related fluorone dyes. The structures of fluorescein, a rhodamine, and two rhodol analogues are shown below.

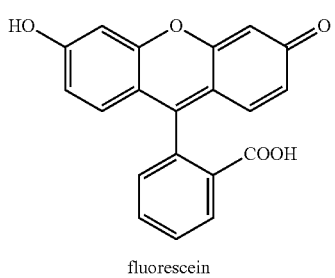

fluorescein

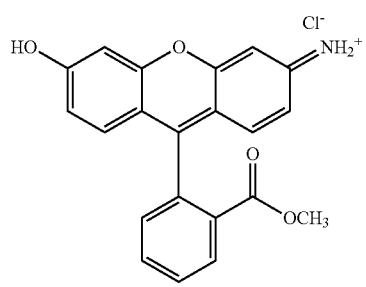

Rhodamine 123

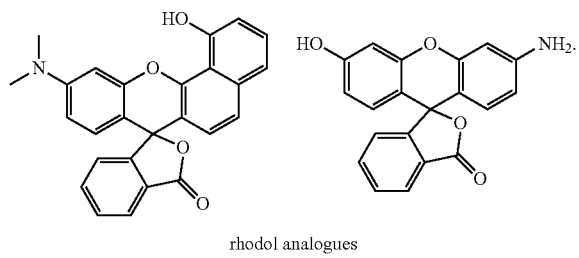

rhodol analogues

A substituent is an atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, an aryl group, a cyclic group, a heteroaryl group or a heterocyclic group.

II. Overview of Representative Embodiments

Embodiments of compounds for selectively detecting thiols such as cysteine, homocysteine, and/or glutathione are disclosed. Also disclosed are embodiments of methods and kits for performing the detection. Embodiments of the disclosed compounds when reacted with one or more thiols in solution, particularly cysteine, homocysteine, glutathione, or combinations thereof, produce a change in the solution's absorbance spectrum and/or emission (fluorescence) spectrum.

In one embodiment, the compound has a structure according to (a) Formula I

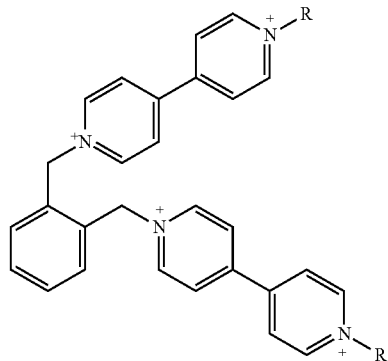

where R is a lower alkyl nitrile, lower alkyl-substituted phenyl, alkenyl, alkynyl, substituted coumarin, acetal, carboxylate group, or a fluorophore; or (b) Formula II

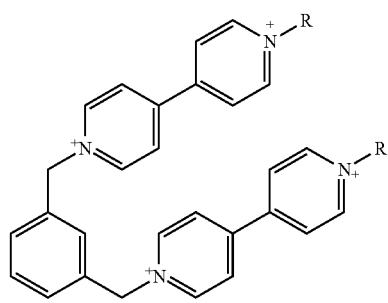

where R is a lower alkyl nitrile, lower alkyl-substituted phenyl, alkenyl, alkynyl, substituted coumarin, acetal, carboxylate group, or a fluorophore; or (c) Formula III

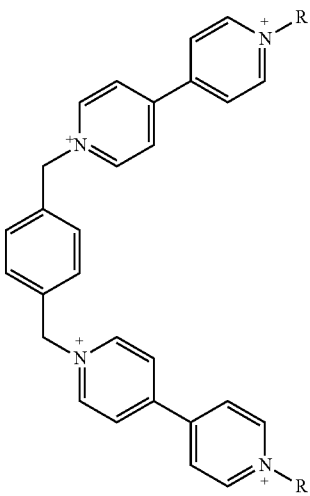

where R is a lower alkyl nitrile, alkenyl, alkynyl, substituted coumarin, acetal, carboxylate group, or a fluorophore.

In any or all of the above embodiments, R may be a fluorophore according to the structure

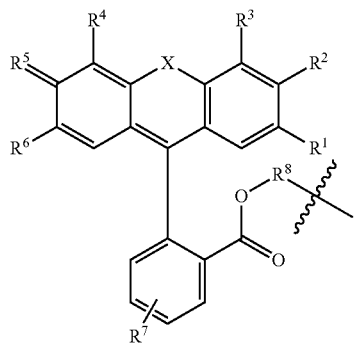

where X is oxygen, sulfur, CH$_2$ or NH; R$^1$, R$^2$, R$^3$, R$^4$, and R$^6$ independently are selected from —H, —OH, lower alkyl, carboxyalkyl, amino, substituted amino, alkoxy, or halogen, or R$^2$ and R$^3$ together may form a substituted or unsubstituted cycloalkyl or aryl; R$^5$ is oxygen, imino, substituted alkyl imino, or substituted or unsubstituted cycloalkyl imino; R$^7$ is —H, alkyl, acyl, carboxyl, nitro, amino, substituted amino; and R$^8$ is absent or alkyl.

In certain embodiments, R is selected from

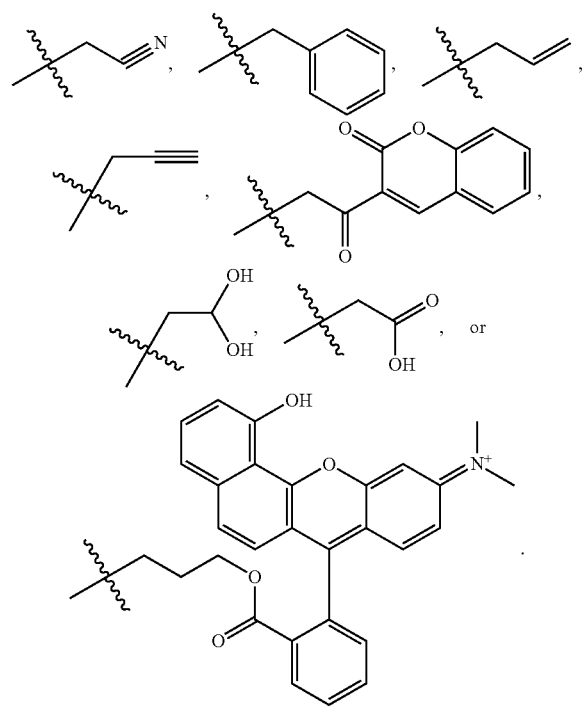

In particular embodiments, the compound is 1',1''-(1,4-phenylenebis(methylene))bis(1-(cyanomethyl)-4,4'-bipyridine-1,1'-diium)bromide, 1',1''-(1,3-phenylenebis(methylene))bis(1-(cyanomethyl)-4,4'-bipyridine-1,1'-diium) bromide, 1',1''-(1,2-phenylenebis(methylene))bis(1-(cyanomethyl)-4,4'-bipyridine-1,1'-diium)bromide, 1',1''-(1,4-phenylenebis(methylene))bis(1-allyl-4,4'-bipyridine-1,1'-diium)bromide, 1',1''-(1,4-phenylenebis(methylene))bis(1-propargyl-1-4,4'-bipyridine-1,1'-diium)bromide, 1',1''-(1,4-phenylenebis(methylene))bis(1-(2-oxo-2-(2-oxo-2H-chromen-3-yl)ethyl)-4,4'-bipyridine-1,1'-diium)bromide, 1',1''-(1,4-phenylenebis(methylene))bis(1-(2,2-dihydroxyethyl)-4,4'-bipyridine-1,1'-diium)bromide, 1',1''-(1,4-phenylenebis(methylene))bis(1-(carboxymethyl)-4,4'-bipyridine-1,1'-diium)bromide, or mono(1',1''-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide.

In one embodiment, a method for detecting a thiol includes forming a solution by combining a sample comprising a thiol with a compound having Formula I, Formula II, or Formula III as described above, allowing a reaction between the thiol and the compound in the solution to proceed for an effective period of time to a produce a detectable change in the solution's absorbance spectrum, emission spectrum, or both, where the change indicates that the thiol is present, and detecting the change.

In some embodiments, the thiol is cysteine, homocysteine, glutathione, or a combination thereof. In any or all of the above embodiments, the compound may be 1',1''-(1,4-phenylenebis(methylene))bis(1-(cyanomethyl)-4,4'-bipyridine-1,1'-diium)bromide, 1',1''-(1,3-phenylenebis(methylene))bis(1-(cyanomethyl)-4,4'-bipyridine-1,1'-diium)bromide, 1',1''-(1,2-phenylenebis(methylene))bis(1-(cyanomethyl)-4,4'-bipyridine-1,1'-diium)bromide, 1',1''-(1,4-phenylenebis(methylene))bis(1-(benzyl)-4,4'-bipyridine-1,1'-diium) bromide, 1',1''-(1,4-phenylenebis(methylene))bis(1-allyl-4,4'-bipyridine-1,1'-diium)bromide, 1',1''-(1,4-phenylenebis(methylene))bis(1-propargyl-1-4,4'-bipyridine-1,1'-diium) bromide, 1',1''-(1,4-phenylenebis(methylene))bis(1-(2-oxo-2-(2-oxo-2H-chromen-3-yl)ethyl)-4,4'-bipyridine-1,1'-diium)bromide, 1',1''-(1,4-phenylenebis(methylene))bis(1-(2,2-dihydroxyethyl)-4,4'-bipyridine-1,1'-diium)bromide, 1',1''-(1,4-phenylenebis(methylene))bis(1-(carboxymethyl)-4,4'-bipyridine-1,1'-diium)bromide, or mono(1',1''-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide.

In any or all of the above embodiments, the effective period of time may be 1-60 minutes. In some embodiments, the reaction occurs at room temperature and the effective period of time is 1-60 minutes. In some embodiments, the reaction occurs under reflux conditions and the effective period of time is 1-5 minutes.

In any or all of the above embodiments, the solution may further include a buffer selected from HEPES (N'-2-hydroxyethylpiperazine-N'-2-ethanesulfonic acid), MOPS (3-(N-morpholino)propanesulfonic acid), phosphate, and TRIS (tris(hydroxymethyl)-aminomethane) buffers. In some embodiments, the thiol is homocysteine, glutathione, or a combination thereof, the buffer is a phosphate or TRIS buffer, and the compound is 1',1''-(1,4-phenylenebis(methylene))bis(1-(cyanomethyl)-4,4'-bipyridine-1,1'-diium)bromide, 1',1''-(1,3-phenylenebis(methylene))bis(1-(cyanomethyl)-4,4'-bipyridine-1,1'-diium)bromide, 1',1''-(1,4-phenylenebis(methylene))bis(1-(benzyl)-4,4'-bipyridine-1,1'-diium) bromide, 1',1''-(1,4-phenylenebis(methylene))bis(1-allyl-4,4'-bipyridine-1,1'-diium)bromide, 1',1''-(1,4-phenylenebis(methylene))bis(1-(2-oxo-2-(2-oxo-2H-chromen-3-yl)ethyl)-4,4'-bipyridine-1,1'-diium)bromide, or a combination thereof.

In any or all of the above embodiments, a change in the solution's absorbance spectrum may be detected by comparing a color of the solution before reaction with the compound to a color of the solution after reaction with the compound. In any or all of the above embodiments, a change in the solution's absorbance spectrum may be detected by detecting a change in absorbance of the solution at one or more wavelengths after the reaction has proceeded for the effective period of time. In any or all of the above embodiments, a change in the solution's absorbance spectrum may be detected by comparing an absorbance spectrum of the solution at a first time after combining the sample and the compound to an absorbance spectrum of the solution after the reaction has proceeded for the effective period of time.

In any or all of the above embodiments, a change in the solution's emission spectrum may be detected by detecting a change in emission of the solution at one or more wavelengths after the reaction has proceeded for the effective period of time. In any or all of the above embodiments, a change in the solution's emission spectrum may be detected by comparing an emission spectrum of the solution at a first time after combining the sample and the compound to an emission spectrum of the solution after the reaction has proceeded for the effective period of time.

In one embodiment, a kit for detecting a thiol includes at least one compound suitable for selectively detecting a thiol, where the compound has Formula I, Formula II, or Formula III as described above, and at least one buffer in which the compound when combined with the thiol has an absorbance spectrum, an emission spectrum, or both that differs from an absorbance spectrum, an emission spectrum, or both when the thiol is absent. In some embodiments, the thiol is cysteine, homocysteine, glutathione, or a combination thereof.

In any or all of the above embodiments, the at least one compound may be selected from 1',1'''-(1,4-phenylenebis(methylene))bis(1-(cyanomethyl)-4,4'-bipyridine-1,1'-diium)bromide, 1',1'''-(1,3-phenylenebis(methylene))bis(1-(cyanomethyl)-4,4'-bipyridine-1,1'-diium)bromide, 1',1'''-(1,2-phenylenebis(methylene))bis(1-(cyanomethyl)-4,4'-bipyridine-1,1'-diium)bromide, 1',1'''-(1,4-phenylenebis(methylene))bis(1-(benzyl)-4,4'-bipyridine-1,1'-diium) bromide, 1',1'''-(1,4-phenylenebis(methylene))bis(1-allyl-4,4'-bipyridine-1,1'-diium)bromide, 1',1'''-(1,4-phenylenebis(methylene))bis(1-propargyl-1-4,4'-bipyridine-1,1'-diium) bromide, 1',1'''-(1,4-phenylenebis(methylene))bis(1-(2-oxo-2-(2-oxo-2H-chromen-3-yl)ethyl)-4,4'-bipyridine-1,1'-diium)bromide, 1',1'''-(1,4-phenylenebis(methylene))bis(1-(2,2-dihydroxyethyl)-4,4'-bipyridine-1,1'-diium)bromide, or 1',1'''-(1,4-phenylenebis(methylene))bis(1-(carboxymethyl)-4,4'-bipyridine-1,1'-diium)bromide, mono(1',1'''-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium)tetrabromide, or a combination thereof. In some embodiments, the at least one compound is selected from 1',1'''-(1,4-phenylenebis(methylene))bis(1-(cyanomethyl)-4,4'-bipyridine-1,1'-diium)bromide, 1',1'''-(1,3-phenylenebis(methylene))bis(1-(cyanomethyl)-4,4'-bipyridine-1,1'-diium)bromide, 1',1'''-(1,4-phenylenebis(methylene))bis(1-(benzyl)-4,4'-bipyridine-1,1'-diium) bromide, and 1',1'''-(1,4-phenylenebis(methylene))bis(1-allyl-4,4'-bipyridine-1,1'-diium)bromide, 1',1'''-(1,4-phenylenebis(methylene))bis(1-(2-oxo-2-(2-oxo-2H-chromen-3-yl)ethyl)-4,4'-bipyridine-1,1'-diium)bromide, mono(1',1'''-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide, or a combination thereof. In any or all of the above embodiments, the buffer may be a HEPES (N'-2-hydroxyethylpiperazine-N'-2-ethanesulfonic acid), MOPS (3-(N-morpholino)propanesulfonic acid), phosphate, or TRIS (tris(hydroxymethyl)-aminomethane) buffer.

In any or all of the above embodiments, the kit may further include a color comparison chart for evaluating a color change produced by a reaction between (a) the compound and (b) cysteine, homocysteine, glutathione, or a combination thereof. In any or all of the above embodiments, the kit may also include a plurality of disposable containers in which a reaction between the compound and a thiol can be performed. In some embodiments, an amount of the compound effective to undergo a detectable change in the absorbance spectrum, the emission spectrum, or both when reacted with a thiol is premeasured into the plurality of disposable containers.

III. Bridged Viologens

Disclosed herein are embodiments of bridged viologens that selectively detect thiols such as cysteine (Cys), homocysteine (Hcy) and/or glutathione (GSH). As used herein, the term "bridged viologen" refers to a compound having a central portion comprising two viologen moieties bonded to a common structural element, or bridge, such as a dimethylbenzene ring. Various substituents can be attached to the free ends of the viologen moieties, forming bridged viologen compounds having varied properties. In some embodiments, the bridged viologens react with the thiols in a buffered solution to form a colored product and/or undergo a change in absorbance spectrum and/or emission spectrum. Product formation and/or spectral differences can be monitored visually or by spectroscopic methods, e.g., UV-visible or fluorescence spectroscopy. In particular embodiments, a bridged viologen is selective for one or more of Cys, Hcy, and GSH. Selectivity may be demonstrated by formation of a more intensely colored product and/or a different colored product. Selectivity also may be demonstrated by a detectable change in the absorbance spectrum and/or emission spectrum of a solution containing the bridged viologen and the thiol, or by a detectable change in the absorbance and/or fluorescence emission at one or more wavelengths of the solution containing the bridged viologen and the thiol. In certain embodiments, temperature and/or buffer composition affects selectivity of a particular bridged viologen. Viologen selectivity for one or more thiols forms a basis for colorimetric and/or spectrophotometric methods of determining the presence and/or amount of Cys, Hcy, and/or GSH in a sample, such as a biological fluid. Determination can be qualitative (e.g., monitoring a visual change in color or by monitoring a change in the absorbance spectrum and/or emission spectrum before and after reaction) or quantitative (e.g., measuring a change in absorbance or emission at a particular wavelength or wavelengths).

The bridged viologens have the general formula I, II, or III:

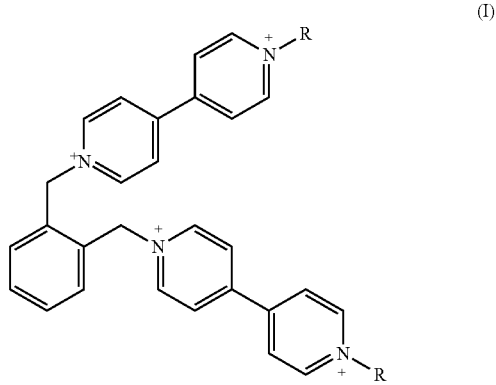

(I)

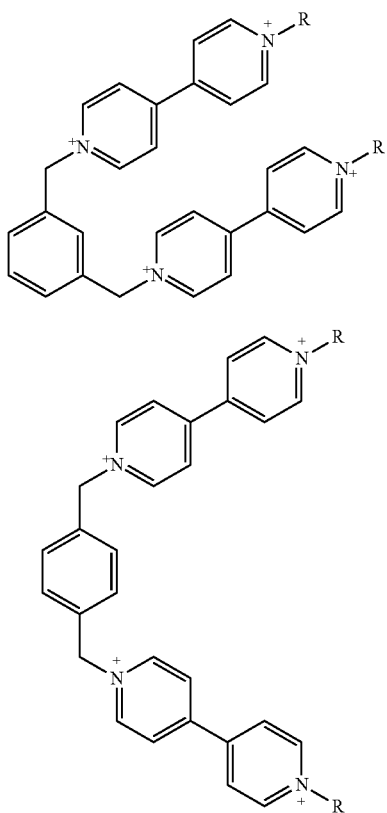

where R is a substituent. In some embodiments, as disclosed herein, the two R substituents are the same. However, in other embodiments, the two R groups may be selected independently. Suitable R substituents include substituted and unsubstituted aliphatic groups, such as substituted and unsubstituted alkanes, alkenes, or alkynes, aryl or heteroaryl groups comprising one or more substituted or unsubstituted aromatic rings and/or heteroaromatic rings, particularly lower aliphatic, aryl, or heteroaryl substituents, wherein substituted lower aliphatic, aryl, or heteroaryl substituents include one or more functional groups including hydroxyl, sulfhydryl, nitrile, amide, hydroxyl, and carbonyl bearing groups, such as ketone, aldehyde, and carboxyl. Suitable R substituents also include fluorophores. In some embodiments, the fluorophores are rhodol analogues according to general formula IV:

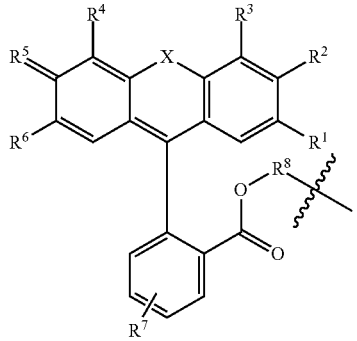

where X is oxygen, sulfur, $CH_2$ or NH; $R^1$, $R^2$, $R^3$, $R^4$, and $R^6$ independently are selected from —H, —OH, lower alkyl, carboxyalkyl, amino, substituted amino, alkoxy, or halogen, or $R^2$ and $R^3$ together may form a substituted or unsubstituted cycloalkyl or aryl; $R^5$ is oxygen, imino, substituted alkyl imino, or substituted or unsubstituted cycloalkyl imino; $R^7$ is —H, alkyl, acyl, carboxyl, nitro, amino, substituted amino; and $R^8$ is absent or alkyl.

In some embodiments, R is a lower alkyl nitrile, lower alkyl-substituted phenyl, alkenyl, alkynyl, substituted coumarin (1-benzopyran-2-one), acetal, carboxylate group, or a compound according to formula IV. In particular embodiments, R is cyanomethyl (—$CH_2C\equiv N$), benzyl (—$CH_2C_6H_5$), allyl (—$CH_2$—CH=$CH_2$), propargyl (—$CH_2$—C≡CH), 1-(2-oxo-2-2H-chromen-3-yl)ethyl, 1-(2,2-dihydroxyethyl) (—$CH_2CH(OH)_2$), 1-carboxymethyl (—$CH_2COOH$), or 3-(2-(10-(dimethylimino)-1-hydroxy-10H-benzo[c]xanthen-7-yl)benzoyloxy)propyl.

Para-, ortho-, and meta-bridged bis-cyanomethyl-viologens were synthesized.

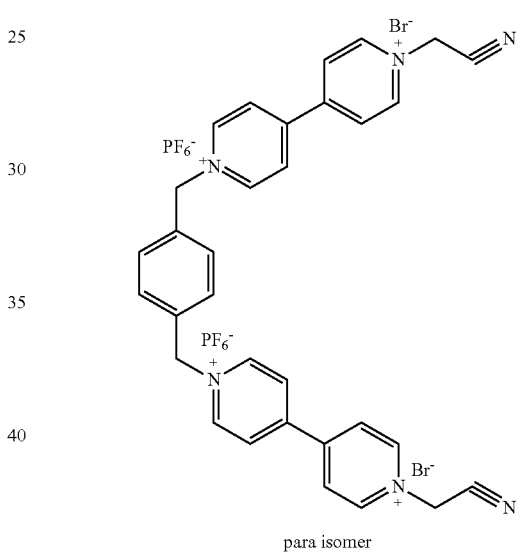

para isomer

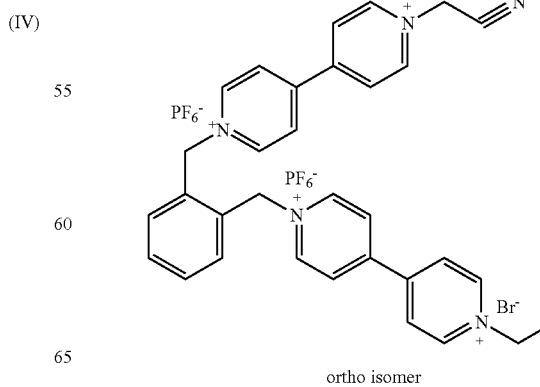

ortho isomer

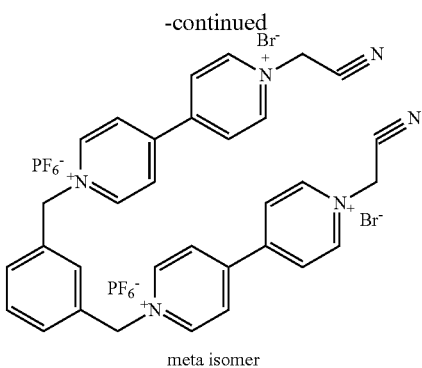

meta isomer

The three isomers have nearly identical UV-vis spectra with a maximum absorbance at 262 nm for all three compounds (FIG. 2).

Figure 4:
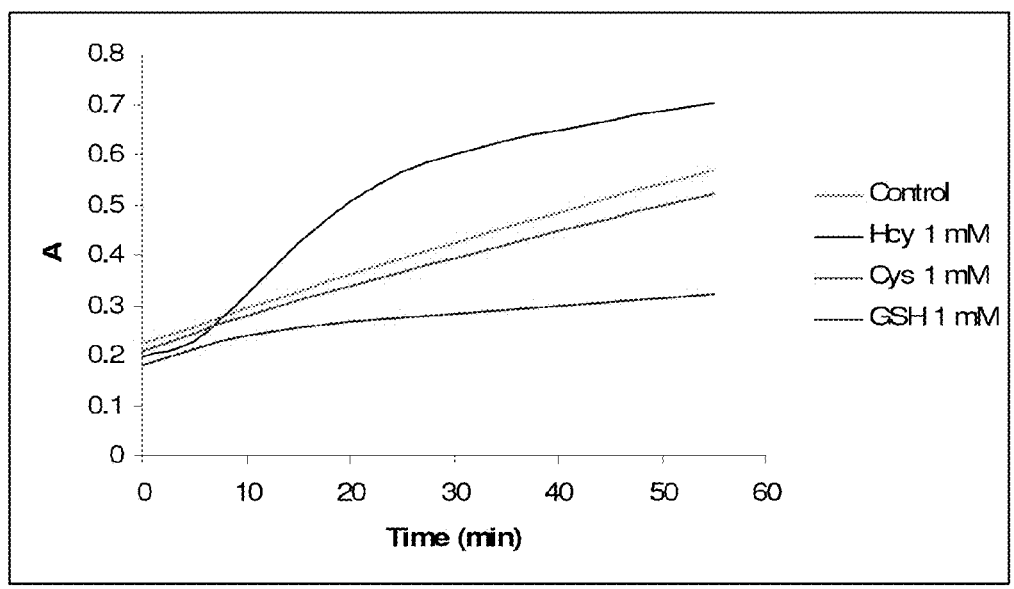
FIG. 4 is a graph of absorbance at 534 nm versus time for the reaction of meta-bridged bis-CN viologen with thiols.
Figure 5:
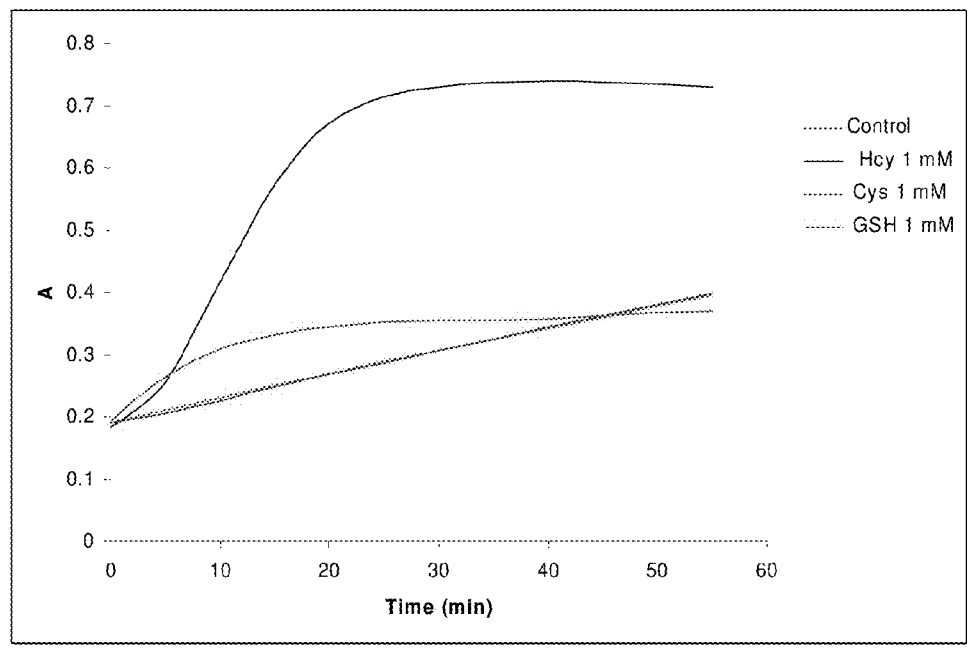
FIG. 5 is a graph of absorbance at 534 nm versus time for the reaction of para-bridged bis-CN viologen with thiols.

The reaction of each isomer with Cys, Hcy, and GSH in 83.3 mM TRIS buffer was investigated by monitoring the change in absorbance at 534 nm as a function of time. As seen in FIGS. 3-5, respectively, the ortho, meta, and para isomers exhibited significant differences in their reactions with the thiols. The ortho isomer demonstrated increased absorbance relative to the control when reacted with GSH and Hcy, with a greater increase seen with GSH. The meta isomer demonstrated increased absorbance with Hcy. Absorbance increased rapidly from about 5 to 20 minutes, and then began to level off. A markedly decreased absorbance relative to the control was seen with GSH. Little or no reaction was seen in the presence of Cys. The para isomer demonstrated a sharp increase in absorbance over about 20 minutes in the presence of Hcy, with absorbance remaining substantially constant after 20 minutes. A more modest increase in absorbance was seen in the presence of GSH with absorbance again flattening out after about 20 minutes. Based on these results, in TRIS buffer the ortho isomer appears to react selectively with GSH and, to a lesser extent, Hcy; the meta isomer appears to react selectively with Hcy and GSH; the para isomer appears to react selectively with Hcy, to a lesser extent with GSH, and has no appreciable reaction with Cys. Hence, in some embodiments, a method for selectively detecting Hcy is performed by reacting a sample that may contain Hcy with meta- or para-bridged bis-CN viologen in TRIS buffer for 1-60 minutes at room temperature. In other embodiments, a method for selectively detecting GSH is performed by reacting a sample that may contain GSH with meta-bridged bis-CN viologen in TRIS buffer for 1-60 minutes at room temperature.

In some embodiments, buffer composition affects the thiol selectivity of a bridged viologen. The influence of the buffer salt on the reaction of para-bridged bis-CN viologen with Cys, Hcy, and GSH at room temperature was investigated. HEPES (N'-2-hydroxyethylpiperazine-N'-2-ethanesulfonic acid), TES (N-tris(hydroxy-methyl)methyl-2-amino-ethane-sulfonic acid), MOPS (3-(N-morpholino)propane-sulfonic acid), phosphate, and TRIS (tris(hydroxymethyl)-aminomethane) buffers were evaluated (FIGS. 10-14, respectively). All buffer concentrations were 8.3 mM. Para-bridged bis-CN viologen demonstrated selectivity (as qualitatively determined by visible color changes) for Hcy in HEPES, MOPS, phosphate and TRIS buffers after 30 minutes. Selectivity for GSH in TRIS was also demonstrated after reaction for 1-30 minutes. Thus, in some embodiments a method for selectively detecting the presence of Hcy is performed in HEPES, MOPS, phosphate, or TRIS buffer with para-bridged bis-CN viologen with determination of Hcy presence after 30 minutes. In another embodiment, a method for selectively detecting the presence of GSH is performed in TRIS buffer with para-bridged bis-CN viologen with determination of GSH presence after 1-30 minutes. In yet another embodiment, a method for selectively detecting the presence of GSH and/or Hcy is performed in TRIS buffer with para-bridged bis-CN viologen with determination of GSH presence after 1 minute and determination of Hcy presence after 30 minutes.

A series of analogues of para-bridged bis-CN viologen was synthesized by alkylation of the hexafluorophosphate salt of the bis-bridged viologen precursor with an excess of the alkyl bromide under reflux conditions in methyl cyanide (MeCN) for 3-12 hours according to the following scheme:

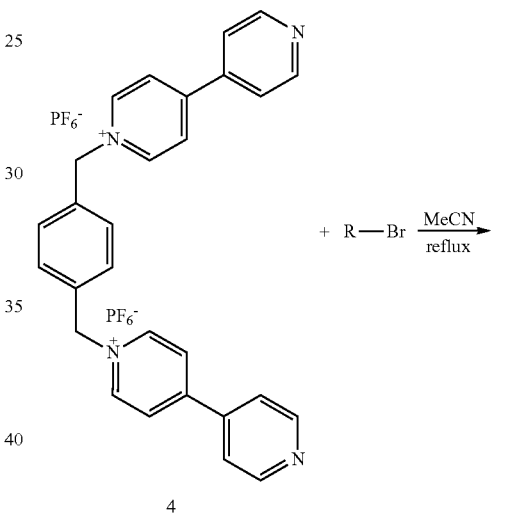

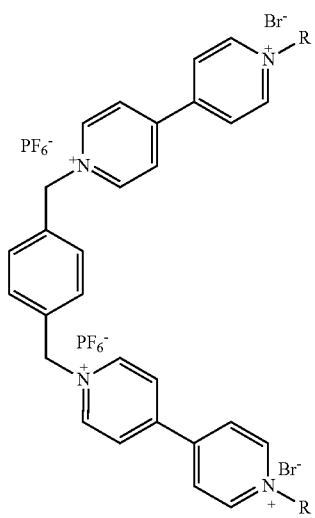

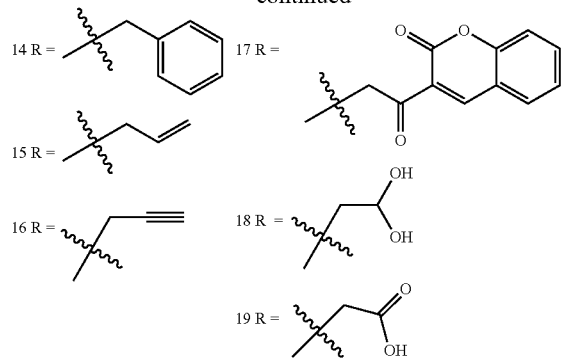

Benzyl, allyl, propargyl, coumarin, acetal, and carboxylate analogues were prepared. Yields for the new analogues ranged from 25-65%.

Each analogue was evaluated for reactions with Cys, Hcy, and GSH in TRIS buffer at room temperature. The benzyl, allyl, and carboxylated analogues did not react with any of the thiols. (See, e.g., FIG. 18.) The propargyl, coumarin, and acetal analogues reacted with all three thiols, but did not show selectivity based on a qualitative evaluation of color change.

Figure 22:
FIG. 22 is a photograph showing the reaction of the para-bridged bis-benzyl viologen with a blank, homocysteine, cysteine, and glutathione after reflux for 1 minute and 5 minutes.
Figure 23:
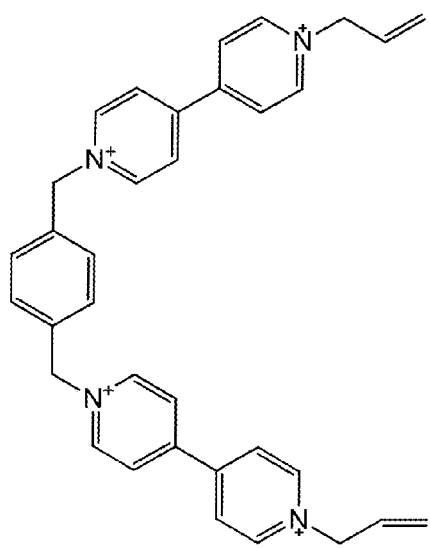
FIG. 23 is a photograph showing the reaction of the para-bridged bis-allyl viologen with a blank, homocysteine, cysteine, and glutathione after reflux for 1 minute and 5 minutes.
Figure 23:
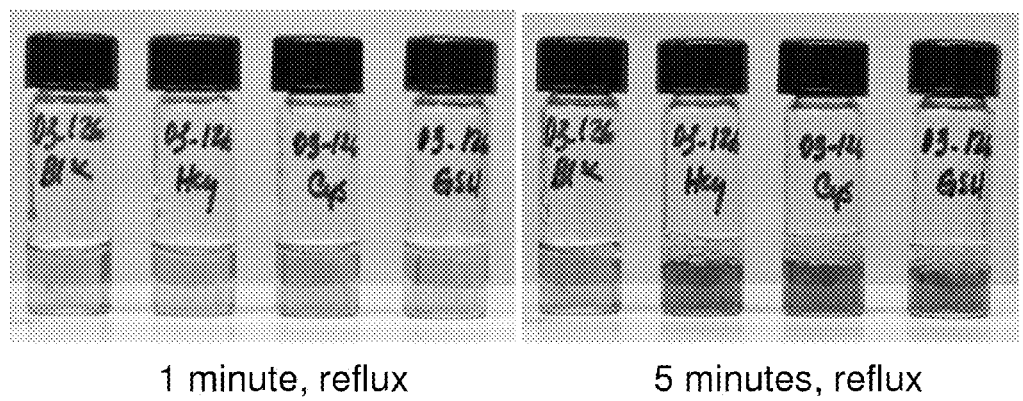

Further investigation of the benzyl and allyl analogues was performed under reflux conditions in TRIS buffer. Under reflux conditions, the benzyl analogue demonstrated strong selectivity for Hcy with formation of a visible blue color (FIG. 22). Samples containing Cys or GSH remained clear. The allyl analogue produced solutions of different color, depending on the thiol used (FIG. 23). The color changes are more pronounced when Hcy or GSH is present. Thus, in one embodiment, a method for selectively detecting Hcy is performed in TRIS buffer with the benzyl analogue (1',1"-(1,4-phenylenebis(methylene))bis(1-(cyanomethyl)-4,4'-bipyridine-1,1'-diium) bromide) in TRIS buffer under reflux conditions. In another embodiment, a method for determining the presence of Hcy and/or GSH is performed in TRIS buffer with the allyl analogue (1',1"-(1,4-phenylenebis(methylene)) bis(1-allyl-4,4'-bipyridine-1,1'-diium)bromide) under reflux conditions.

Initial investigation of the para-coumarin analogue at a concentration of 6 mM showed no selectivity. However, at a reduced concentration of 1 mM in TRIS buffer, the coumarin analogue produced deep purple solutions with Hcy and Cys and a pale pink solution with GSH within five minutes at room temperature, thereby demonstrating GSH selectivity. Thus, in one embodiment, a method for selectively detecting GSH is performed in TRIS buffer with the coumarin analogue (1',1"-(1,4-phenylenebis-(methylene))bis(1-(2-oxo-2-(2-oxo-2H-chromen-3-yl)ethyl)-4,4'-bipyridine-1,1'-diium) bromide) at room temperature.

Table 1 summarizes the thiol selectivity of the evaluated analogues.

TABLE 1

| Compound/Buffer | Hcy room temp. | Hcy re-flux | Cys room temp. | Cys re-flux | GSH room temp. | GSH re-flux |
|---|---|---|---|---|---|---|
| m-cyano isomer, 9* 83.3 mM TRIS buffer pH 7.0 | X | | | | X | |
| p-cyano isomer, 5 83.3 mM TRIS buffer pH 7.0 | X | | | | | |
| p-cyano isomer, 5 8.3 mM Phosphate buffer | X | | | | | |
| p-cyano isomer, 5 8.3 mM TRIS buffer pH 7.0 | X (after 30 min rxn) | | | | X (after 1 min rxn) | |
| p-benzyl analogue, 14 83.3 mM M TRIS buffer pH 7.0 | | X | | | | |
| p-allyl analogue, 15 83.3 mM M TRIS buffer pH 7.0 | | X | | | | X |
| p-coumarin analogue, 17 83.3 mM M TRIS buffer pH 7.0 | | | | | X (after 5 min rxn) | |

*Numbers refer to compounds in Schemes 1-4 (Examples 1-2).

Figure 28:
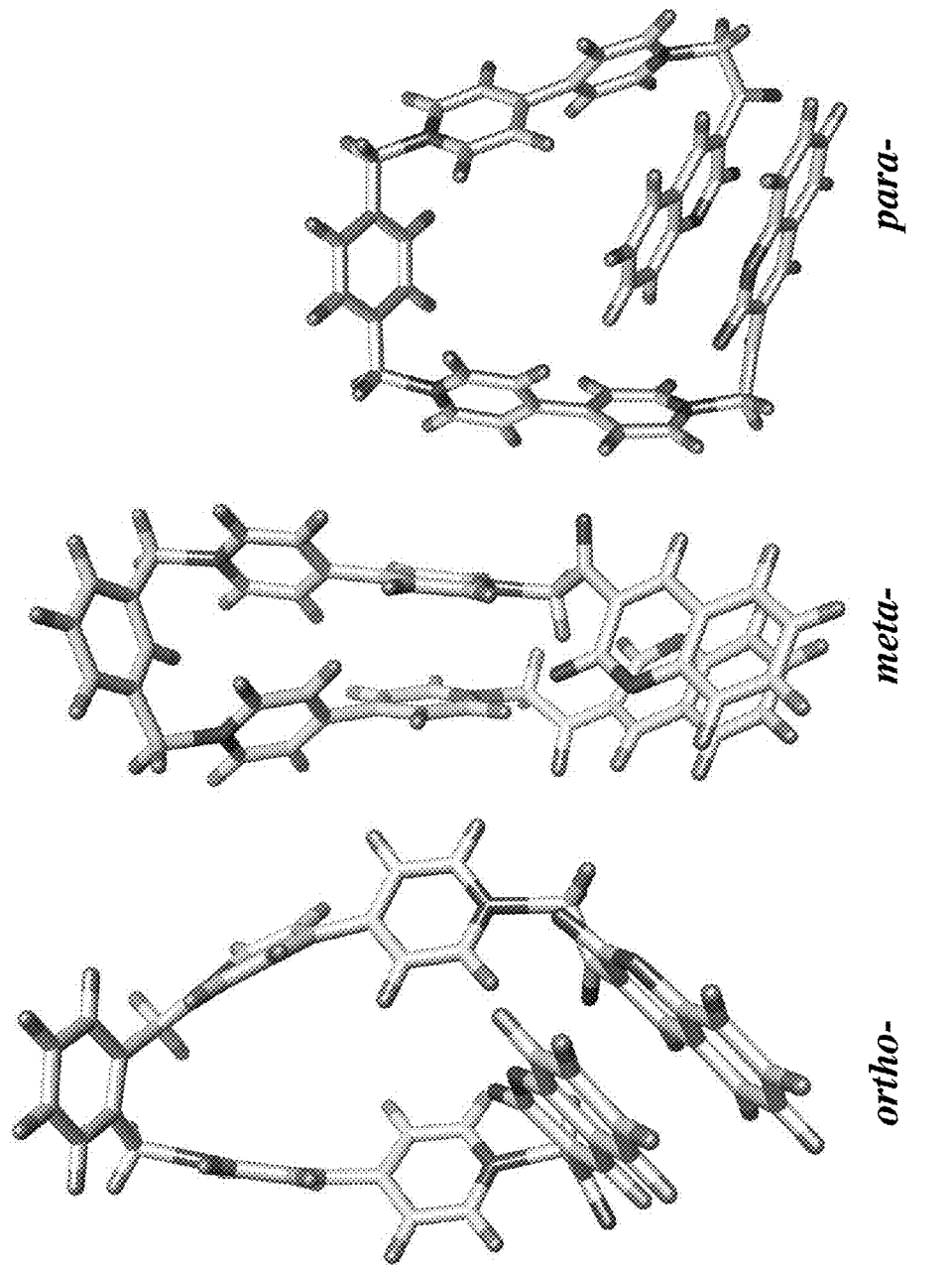
FIG. 28 shows the energy-minimized structures and π-πstacking of single bridged ortho-, meta- and para-bis coumarin viologen analogues.
Figure 29:
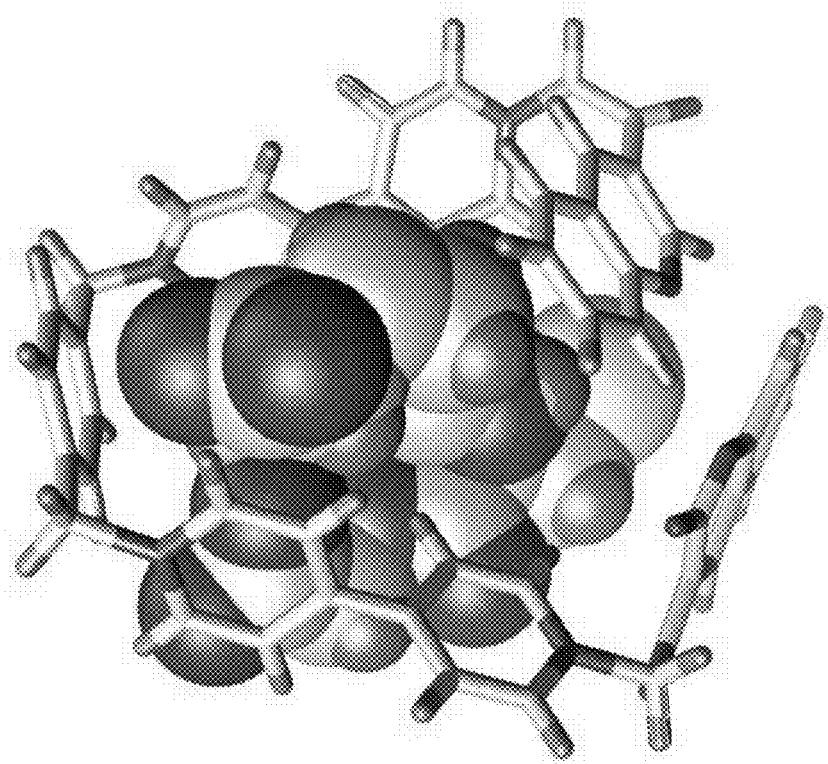
FIG. 29 is the energy-minimized structure of a supramolecular assembly of glutathione and the para-bis coumarin viologen.

It is hypothesized that a supramolecular assembly-type mechanism may be involved in the absorbance and/or emission (fluorescence) spectrum changes observed between the reaction of glutathione and certain embodiments of the bridged viologens in solution, particularly embodiments wherein the bridged viologen includes a fluorophore. In some embodiments, a fluorophore conjugated to the bridged viologen backbone loses its fluorescence capability. It is thought that the viologen may accept electrons from the fluorophore, thereby quenching the fluorescence. FIG. 28 illustrates the energy-minimized structures of ortho-, meta-, and para-bis coumarin analogues. Each structure demonstrates π-π stacking between the two coumarin moieties. However, only the para-structure forms a cavity into which a glutathione molecule may fit. FIG. 29 illustrates a potential supramolecular assembly formed with GSH and the p-bis coumarin analogue. It is anticipated that insertion of the GSH into the cavity will disrupt the π-π stacking. Furthermore, as the bridged viologen analogue folds around the GSH molecule, regions of negative charge in the GSH molecule may align with positive charge centers in the coumarin moieties, thereby restoring the fluorescence capability of the coumarin moieties via a charge transfer mechanism. Thus, in certain embodiments, glutathione may be detected by measuring fluorescence of particular embodiments of the disclosed bridged viologen analogues.

It is anticipated that embodiments of the disclosed bridged viologen analogues will be useful for detecting thiols in bodily fluids such as blood. Utility will be enhanced if the compounds can be used to detect thiols in blood samples with little or no separation or purification of the thiols from the blood sample. Thus, compounds that can be detected at wavelengths other than those absorbed or emitted by blood are desirable. Of particular interest are near-infrared dyes that can be coupled to the bridged viologen backbones, i.e., general formulas I-III. In some embodiments, the near-infrared dye is a fluorophore. One example of a near-infrared dye that may be suitable is a rhodol analogue (shown below), which can be coupled to a bridged viologen via the oxygen atom in the 5-membered ring (see also Scheme 5, Example 6, and FIGS. 30-32).

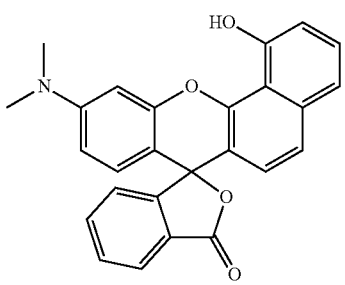

The 5-membered ring can be opened to form a methyl ester derivative, which can be coupled to a bridged viologen.

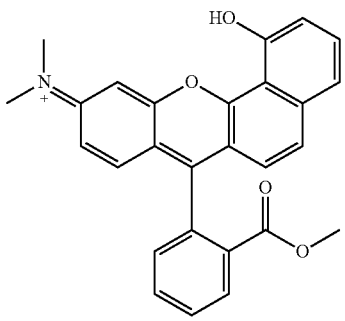

The absorbance and fluorescence spectra of the rhodol analogue typically are pH dependent. For example, the absorbance maximum for this ester derivative in 0.1M NaOH is 620 nm and the emission maximum in same solvent is 770 nm. The Stokes shift in this solvent is 150 nm (3142 cm$^{-1}$).

III. Kits

Kits are also a feature of this disclosure. Embodiments of the kits include a) at least one compound suitable for selectively detecting cysteine, homocysteine, glutathione, or a mixture thereof, and b) at least one buffer in which the compound when combined with Cys, Hcy, GSH, or a mixture thereof to form a solution will undergo a change in its absorbance spectrum and/or emission spectrum compared to the compound in the buffer solution in the absence of Cys, Hcy, and GSH. The kits also may include one or more containers, such as a disposable test tube or cuvette, in which the detection can be performed. The kits may further include instructions for performing the detection. In some embodiments, the kits include a color comparison chart for evaluating a color change to determine whether a given thiol is present. In some embodiments, the kits include control samples of Cys, Hcy, and/or GSH. Typically the control samples are provided in solid form.

In some embodiments of the kits, the compound is provided as a solid, and the buffer is provided in liquid form. The buffer may be provided at a concentration suitable for detecting Cys, Hcy, GSH, or a mixture thereof. Alternatively, the buffer may be provided as a concentrated solution, which is subsequently diluted prior to use. In certain embodiments, the compound may be premeasured into one or more containers (e.g., test tubes or cuvettes), and the detection is subsequently performed by adding the buffer and test sample to the container.

IV. Examples

Example 1

Para-, Ortho-, and Meta-Bridged bis-CN Viologens

Para-bridged bis-CN viologen (1',1"-(1,4-phenylenebis(methylene))bis(1-(cyanomethyl)-4,4'-bipyridine-1,1'-diium)bromide) was synthesized according to Scheme 1:

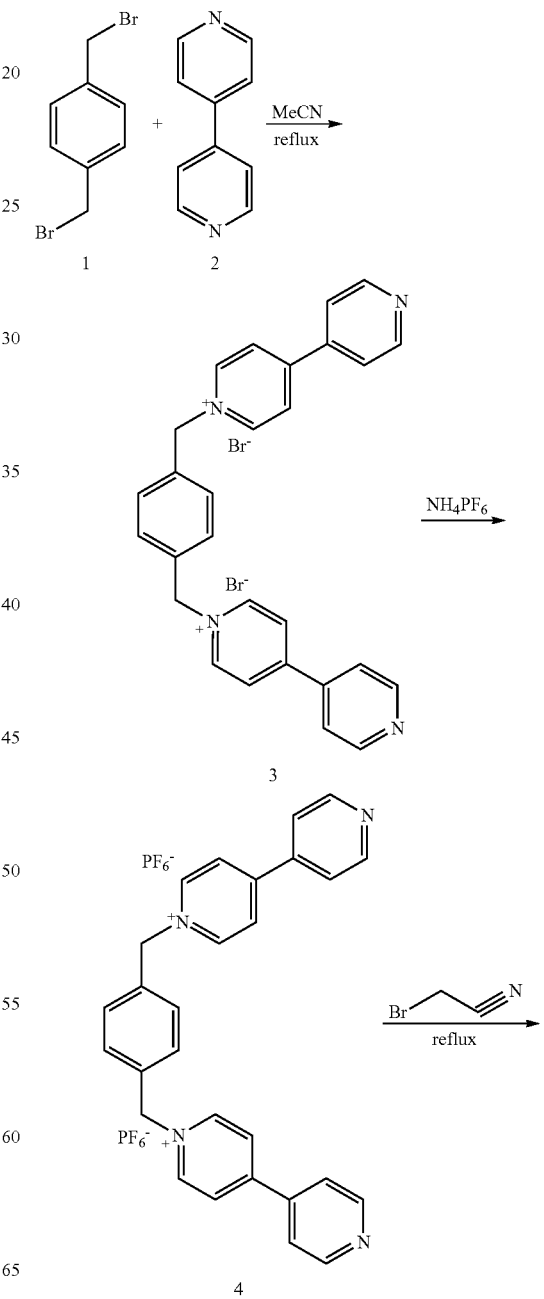

Scheme 1

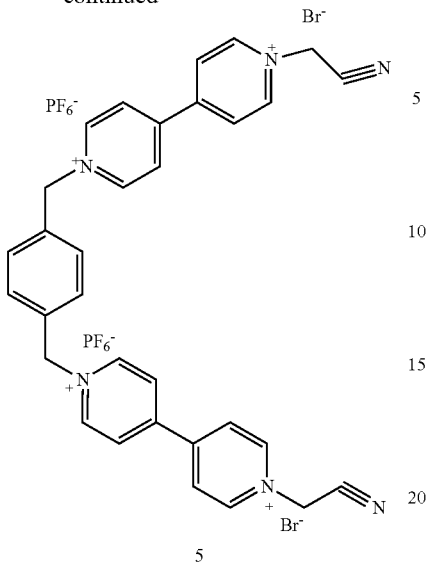

1',1'''-(1,4-phenylenebis(methylene))bis(1-(cyanomethyl)-4,4'-bipyridine-1,1'-diium)bromide, 5

Bipyridine (16.66 g, 106.65 mmol) was dissolved in 125 mL of acetonitrile and the solution was brought to reflux. Next, p-bis-(bromo-methyl)benzene (5 g, 18.94 mmol) was dissolved in 300 mL of acetonitrile. This solution was added to the bipyridine refluxing solution during one hour. After complete addition of the p-bis-(bromo-methyl)benzene solution, the mixture was refluxed for an additional 24 h. The precipitate formed was filtered and washed with acetonitrile (2×50 mL), and air dried. The single bridged viologen 3 was obtained as a pale yellow solid. Yield 10.5 g, 96%. $^1$H NMR (DMSO-$d_6$, 400 MHz): δ (ppm) 9.4-9.41 (4H, d), 8.85-8.86 (4H, d), 8.65-8.67 (4H, d), 8.00-8.01 (4H, d), 7.74 (4H, s), 5.94 (4H, s).

Compound 3 (3 g, 5.3 mmol) was suspended in 30 mL of water, and the mixture was heated until complete dissolution of the precipitate. 20 mL of 1 M NH$_4$PF$_6$ was added slowly. The mixture was allowed to cool down to room temperature, and filtered; the pale yellow precipitate was washed with water (3×50 mL), and dried under vacuum. Yield 3.426 g, 93%. $^1$H NMR (DMSO-$d_6$, 400 MHz): δ (ppm) 9.32-9.34 (4H, d), 8.86-8.87 (4H, d), 8.63-8.64 (4H, d), 7.99-8.00 (4H, d) 7.66 (4H, s), 5.88 (4H, s).

Bromoacetonitrile (7.807 g, 65.09 mmol) was dissolved in 40 mL of acetonitrile and the solution was brought to reflux. The hexafluorophosphate salt 4 (4 g, 5.66 mmol) was dissolved in 200 mL of acetonitrile and added within 1 h to the bromoacetonitrile refluxing solution. After complete addition of the hexafluorophosphate solution, the mixture was refluxed for an additional 12 h. The mixture was allowed to cool down to room temperature. The yellow precipitate was filtered and washed with cold acetonitrile (2×50 mL), then dried under vacuum. Yield 1.61 g, 35%. $^1$H NMR (DMSO-$d_6$, 400 MHz): δ (ppm) 9.59 (4H, d), 9.59 (4H, d), 8.86-8.87 (4H, d), 8.82-8.84 (4H, d), 7.75 (4H, s), 6.10 (4H, s), 6.01 (4H, s). $^{13}$C NMR (DMSO-$d_6$, 100 MHz): δ (ppm) 150.11, 148.58, 146.02, 145.50, 134.85, 129.54, 127.03, 126.84, 113.65, 62.46, 47.43.

Meta-bridged bis-CN viologen (1',1'''-(1,3-phenylenebis(methylene))bis(1-(cyanomethyl)-4,4'-bipyridine-1,1'-diium)bromide) was synthesized according to Scheme 2 using the same general procedure as Scheme 1, with meta-bis-(chloro-methyl)benzene used in place of compound 1:

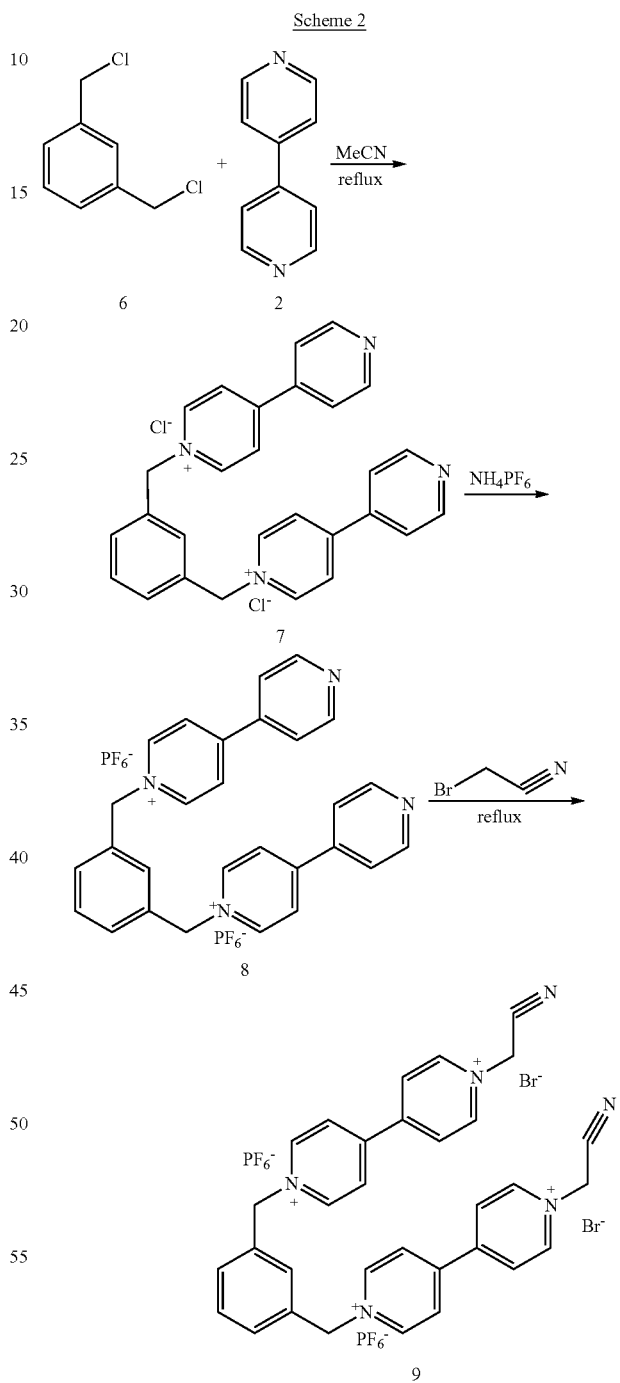

1',1'''-(1,3-phenylenebis(methylene))bis(1-(cyanomethyl)-4,4'-bipyridine-1,1'-diium)bromide, 9

Overall yield (3 steps), 20% $^1$H NMR (D$_2$O, 400 MHz): δ (ppm) 9.36-9.38 (2H, d), 9.26-9.27 (2H, d), 9.21-9.25 (2H, d), 8.73-8.75 (2H, d), 8.65-8.66 (2H, d), 8.60-8.62 (2H, d), 7.67-7.70 (4H, m), 6.06 (4H, s), 6.01 (4H, s). $^{13}$C NMR (D$_2$O, 100 MHz): δ (ppm) 154.91, 153.27, 152.85, 149.02, 148.59, 148.54, 148.49, 136.44, 136.43, 136.39, 136.38, 133.85, 133.81, 133.77, 133.69, 133.06, 133.04, 130.54, 130.35, 130.21, 115.55, 67.14, 67.05.

Ortho-bridged bis-CN viologen (1',1"-(1,2-phenylenebis(methylene))bis(1-(cyanomethyl)-4,4'-bipyridine-1,1'-diium)bromide) was synthesized according to Scheme 3 using the same general procedure as Scheme 1, with ortho-bis-(bromo-methyl)benzene used in place of compound 1:

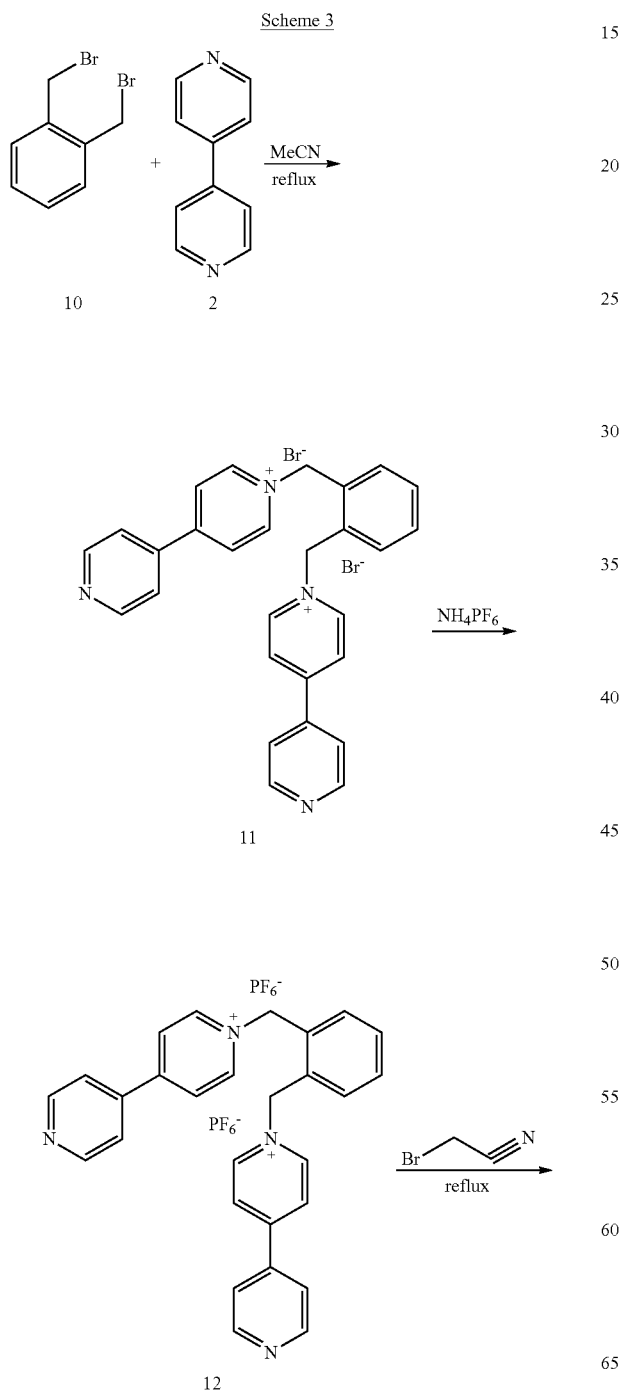

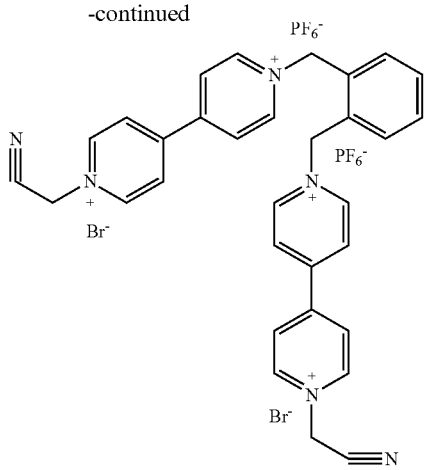

1',1"-(1,2-phenylenebis(methylene))bis(1-(cyanomethyl)-4,4'-bipyridine-1,1'-diium)bromide, 13

Overall yield (3 steps) 7%. $^1$H NMR (D$_2$O, 400 MHz): δ (ppm) 9.34-9.35 (4H, d), 9.18-9.20 (4H, d), 8.73-8.74 (4H, d), 8.67-8.69 (4H, d), 7.66-7.68 (2H, dd), 7.37-7.40 (2H, dd), 6.21 (4H, s). $^{13}$C NMR (D$_2$O, 100 MHz): δ (ppm) 154.87, 153.64, 153.32, 149.23, 149.14, 148.98, 148.90, 148.84, 134.35, 133.86, 133.81, 133.78, 133.63, 130.79, 130.75, 130.66, 130.61, 130.52, 115.61, 64.25, 64.21.

FIG. 2 shows the UV-vis spectra of ortho-, meta-, and para-bis CN viologens, 2×10$^{-5}$ M in water. The spectra of all three compounds show a maximum absorbance at 262 nm.

Each of the analogues was screened for reaction with 1 mM solutions of homocysteine, cysteine, and glutathione in 83.3 mM TRIS buffer, pH 7.0, at room temperature. The reactions were allowed to proceed for 30-60 minutes. The analogues were added to a final concentration of 8 mM.

Figure 6:
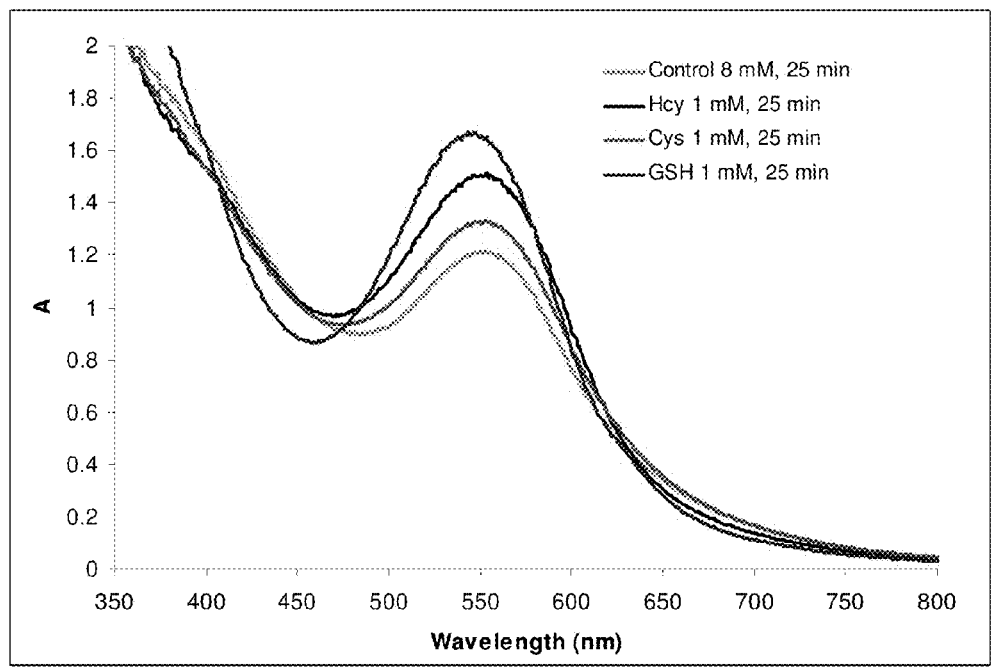
FIG. 6 is the UV-vis spectra for the reaction of ortho-bridged CN viologen with thiols at 25 minutes.
Figure 7:
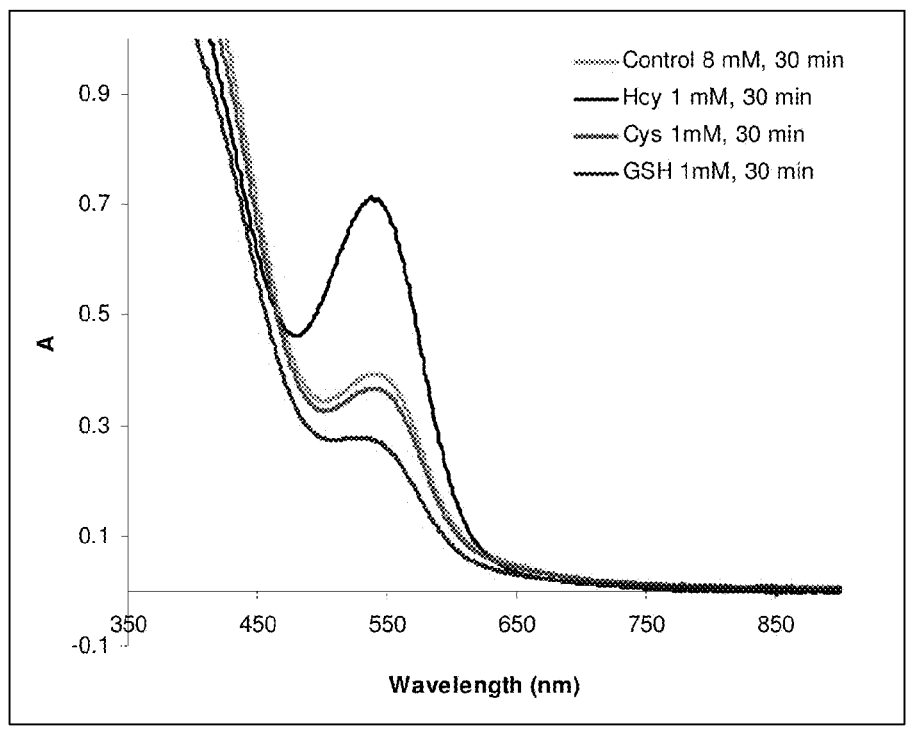
FIG. 7 is the UV-vis spectra for the reaction of meta-bridged CN viologen with thiols at 30 minutes.
Figure 8:
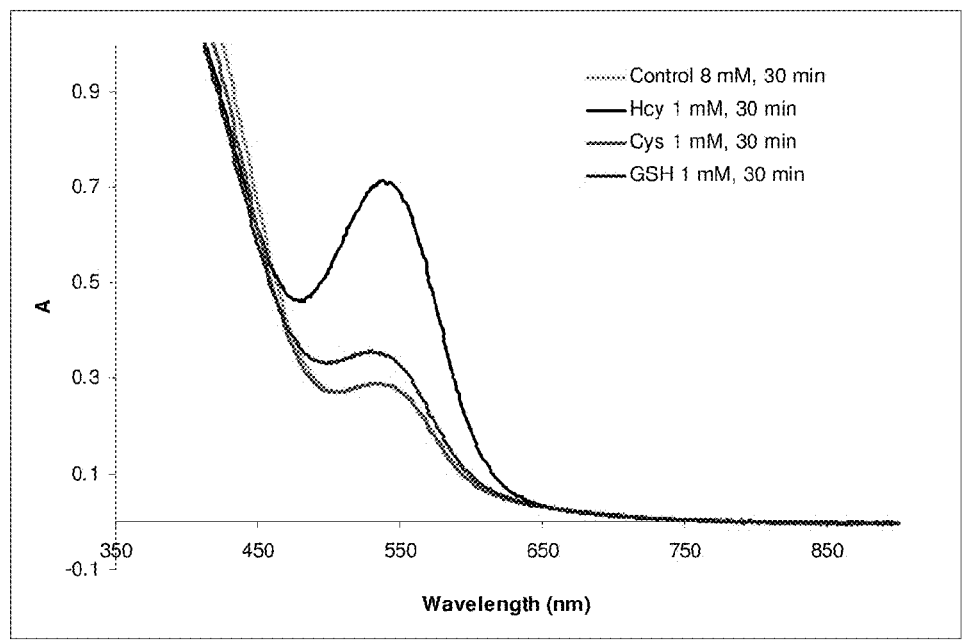
FIG. 8 is the UV-vis spectra for the reaction of para-bridged CN viologen with thiols at 30 minutes.

FIGS. 3-5 show the absorbance at 534 nm for the reaction of the ortho-, meta-, and para-isomers, respectively, with the thiols as a function of time. The change in absorbance at 534 nm is attributed to the formation of a viologen di-radical species. FIG. 6 shows the UV-vis spectra for the reaction of the ortho-isomer with the thiols at 25 minutes. FIGS. 7-8 are UV-vis spectra for the reaction of the meta-, and para-isomers, respectively, with the thiols at 30 minutes.

Figure 9:
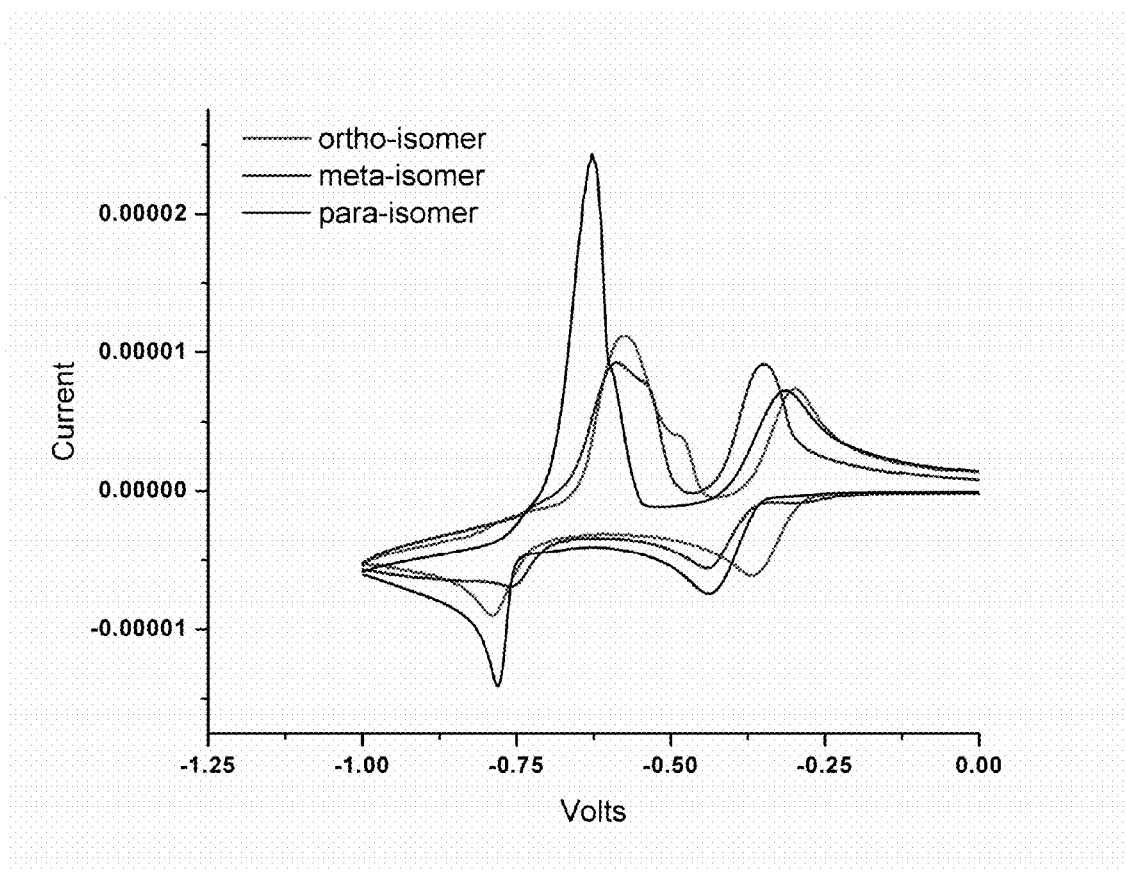
FIG. 9 shows the voltammograms of the para-, ortho-, and meta-bridged bis-CN viologens in 50 mM phosphate buffer, pH 7.0 at 20 mV/s vs. SCE, glassy carbon.
Figure 10:
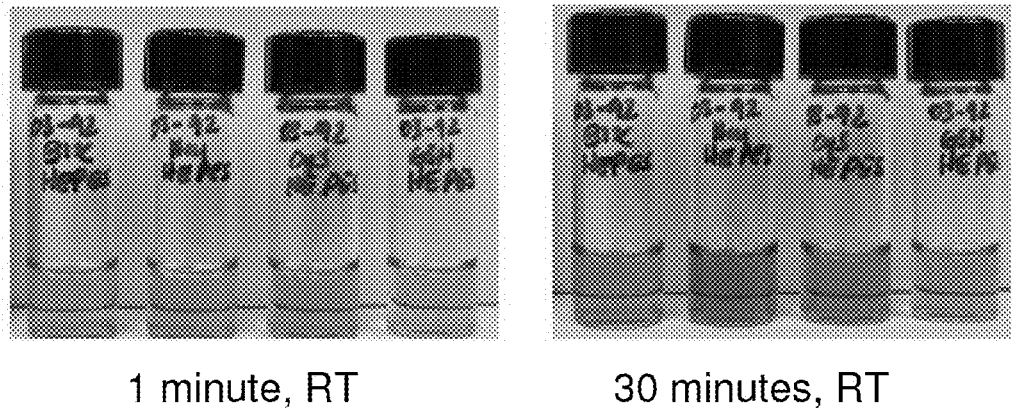
FIG. 10 is a photograph showing the reaction of the para-bridged bis-CN viologen with a blank, homocysteine, cysteine, and glutathione in 8.3 mM HEPES buffer, pH 7.0, at room temperature after 1 minute and 30 minutes.
Figure 11:
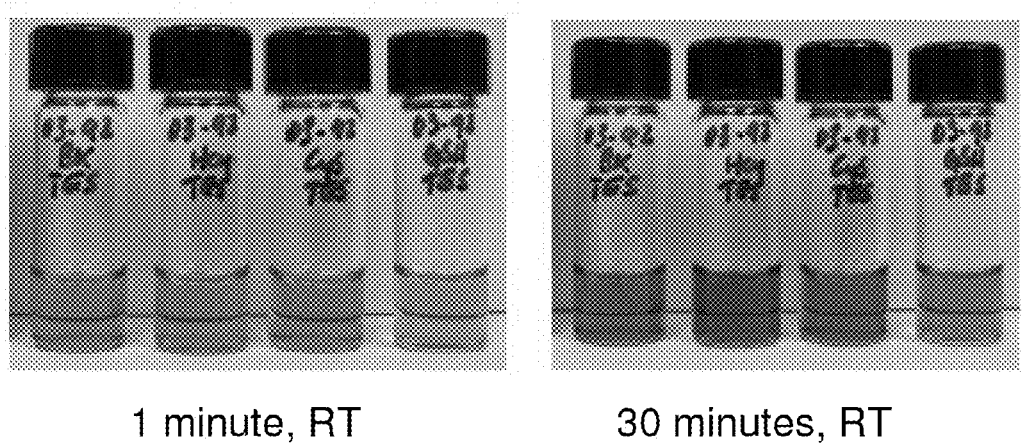
FIG. 11 is a photograph showing the reaction of the para-bridged bis-CN viologen with a blank, homocysteine, cysteine, and glutathione in 8.3 mM TES buffer, pH 7.0, at room temperature after 1 minute and 30 minutes.
Figure 12:
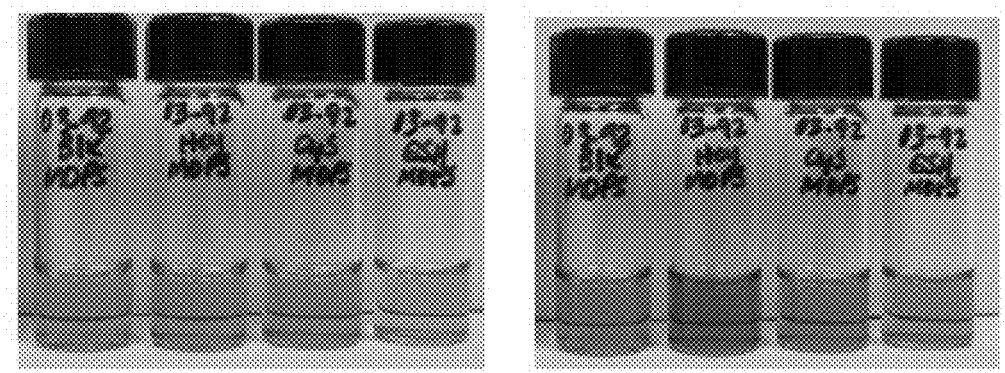
FIG. 12 is a photograph showing the reaction of the para-bridged bis-CN viologen with a blank, homocysteine, cysteine, and glutathione in 8.3 mM MOPS buffer, pH 7.0, at room temperature after 1 minute and 30 minutes.
Figure 13:
FIG. 13 is a photograph showing the reaction of the para-bridged bis-CN viologen with a blank, homocysteine, cysteine, and glutathione in 8.3 mM phosphate buffer, pH 7.0, at room temperature after 1 minute and 30 minutes.
Figure 14:
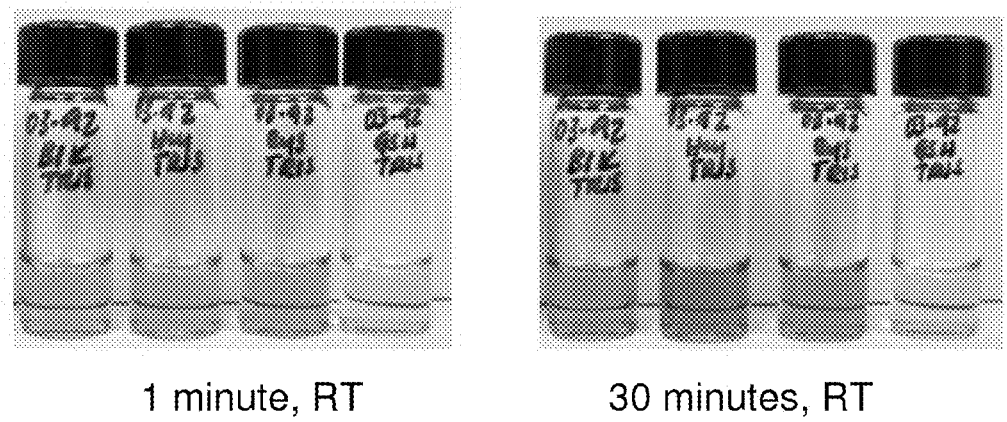
FIG. 14 is a photograph showing the reaction of the para-bridged bis-CN viologen with a blank, homocysteine, cysteine, and glutathione in 8.3 mM TRIS buffer, pH 7.0, at room temperature after 1 minute and 30 minutes.

Cyclic voltammetry of the ortho-, meta-, and para-isomers in 50 mM phosphate buffer, pH 7.0, at 20 mV/s vs. SCE, glassy carbon, showed that these tetracations behave as two-step redox systems with similar patterns (FIG. 9). However, differences in their current were observed, and since the voltammograms are not completely symmetric, it is considered that the reversibility may be disturbed by adsorption and slow charge transfer, as has been reported. The voltages at which oxidation and reduction peaks were observed are shown in Table 2.

TABLE 2

| Compound | Oxidation (Volts) | | Reduction (Volts) | |
|---|---|---|---|---|
| o-isomer | 0.570 | 0.290 | 0.796 | 0.367 |
| m-isomer | 0.580 | 0.350 | 0.752 | 0.436 |
| p-isomer | 0.622 | 0.316 | 0.792 | 0.438 |

The influence of the buffer salt on the reaction of the para-isomer with Hcy, Cys, and GSH at room temperature was evaluated. The buffer concentration (8.3 mM) and pH (7.0) were kept constant. HEPES (N'-2-hydroxyethylpiperazine-N'-2-ethanesulfonic acid), TES (N-tris(hydroxymethyl)methyl-2-amino-ethanesulfonic acid), MOPS (3-(N-morpholino)propanesulfonic acid), phosphate, and TRIS (tris(hydroxymethyl)-aminomethane) buffers were evaluated (FIGS. 10-14, respectively). The thiol concentrations were 1 mM. The results showed that para-bridged bis-CN viologen reacts selectively with Hcy in HEPES, MOPS, phosphate and TRIS buffers. Better results in terms of color development were seen with the phosphate and TRIS buffers. GSH selectivity was seen in TRIS buffer.

Figure 15:
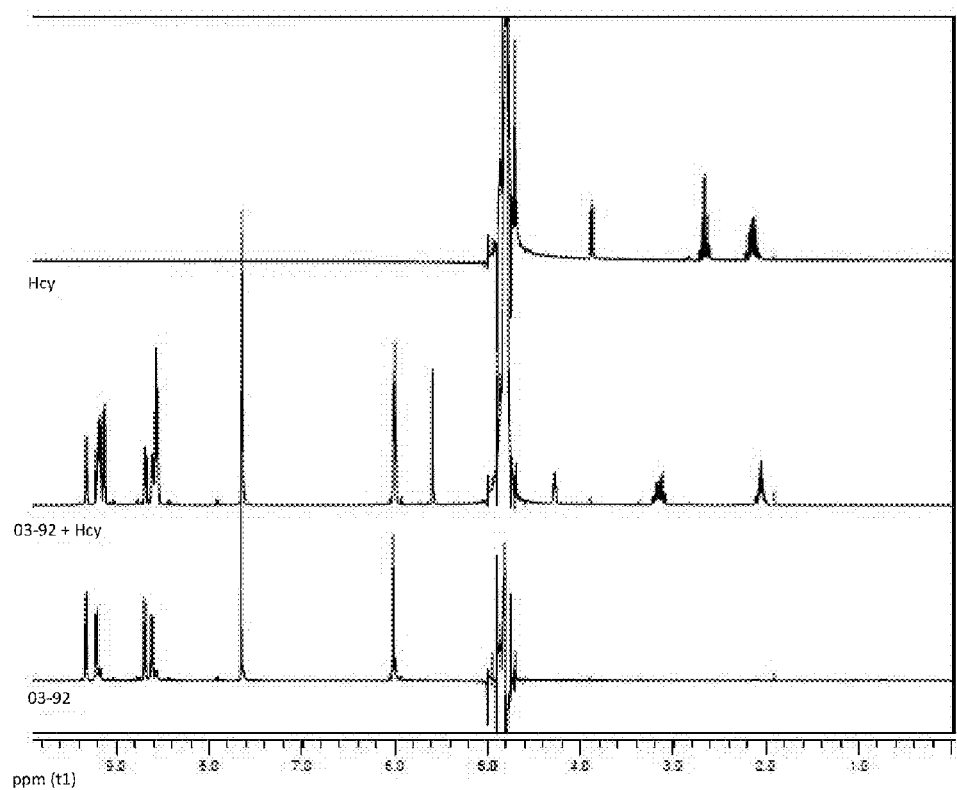
FIG. 15 is a $^1H$ NMR spectrum of the reaction of the para-bridged bis-CN viologen with 10 mM homocysteine in 50 mM phosphate buffer pH 7.0:$D_2O$ 90:10, at room temperature after 1 hour.
Figure 16:
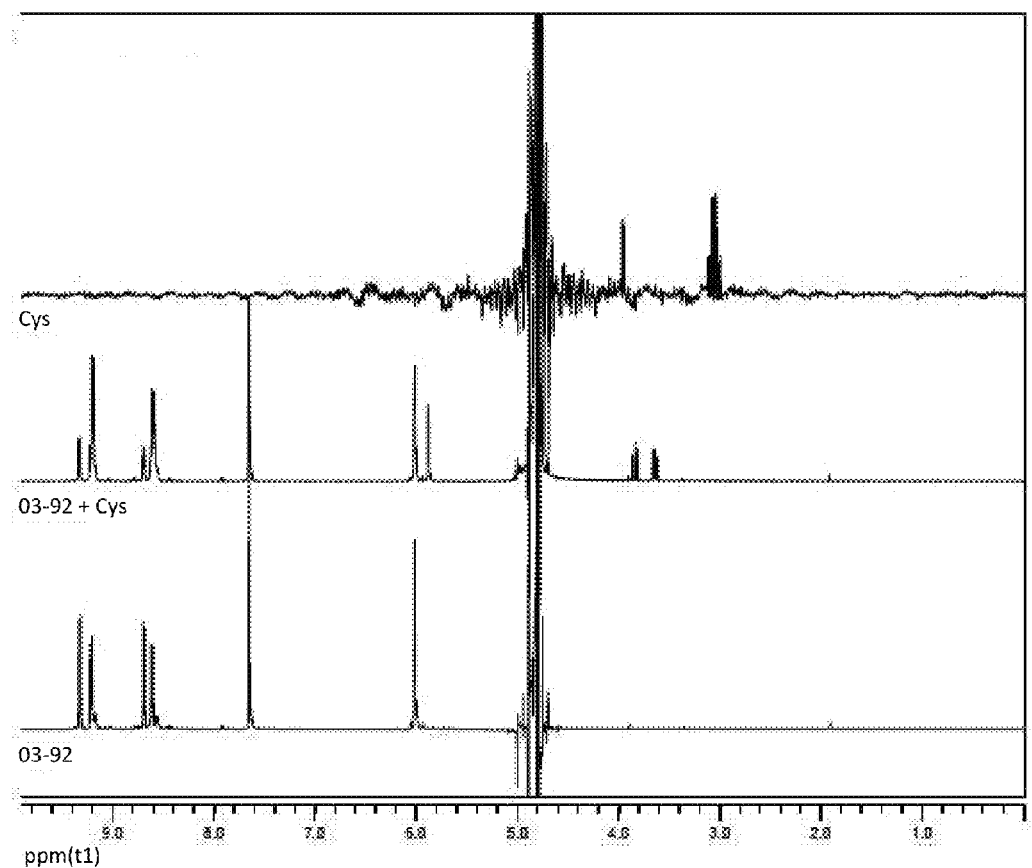
FIG. 16 is a $^1H$ NMR spectrum of the reaction of the para-bridged bis-CN viologen with 10 mM cysteine in 50 mM phosphate buffer pH 7.0:$D_2O$ 90:10, at room temperature after 1 hour.
Figure 17:
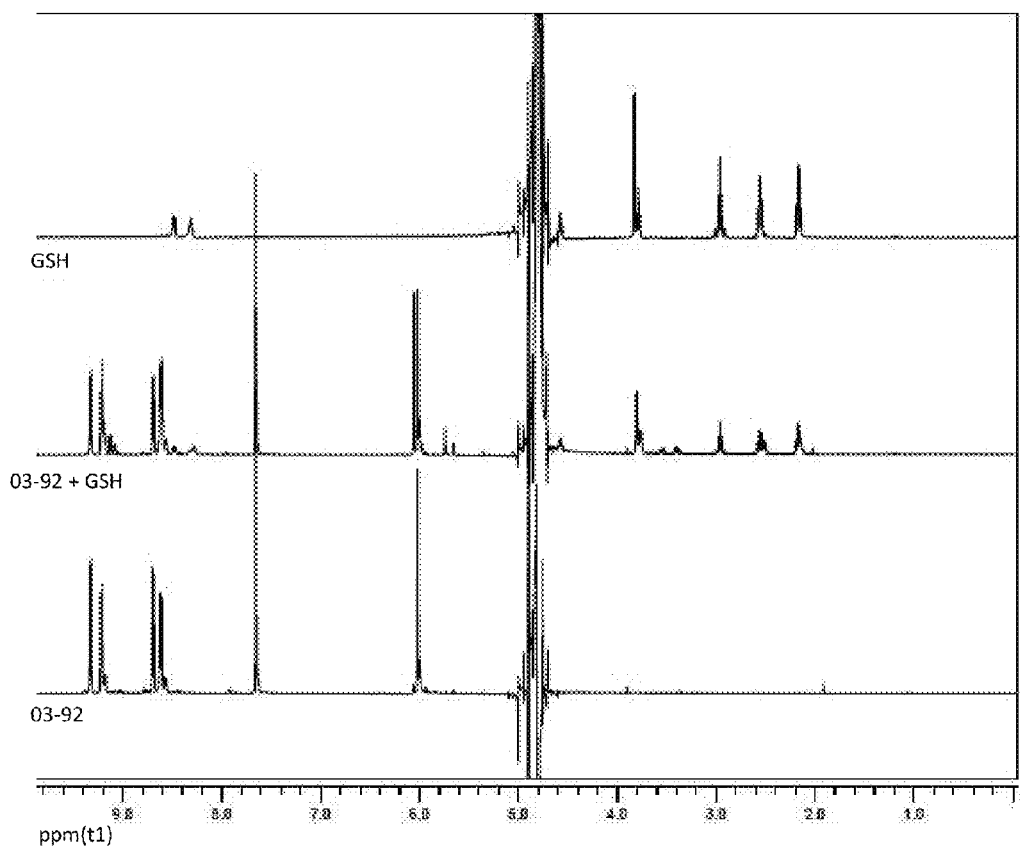
FIG. 17 is a $^1H$ NMR spectrum of the reaction of the para-bridged bis-CN viologen with 10 mM glutathione in 50 mM phosphate buffer pH 7.0:$D_2O$ 90:10, at room temperature after 1 hour.

The reaction of the para-isomer with 10 mM Hcy, Cys, and GSH in 50 mM phosphate buffer, pH 7, at room temperature, was evaluated after 1 hour by $^1$H NMR. The NMR spectra showed that, in the case of Hcy (FIG. 15) and Cys (FIG. 16), the α-C—H, and CH, protons were shifted downfield, and that only the protons from the pyridine moieties of the viologen were affected, giving new upfield signals. No major changes were observed for the reaction of GSH with compound 5 (FIG. 17).

Example 2

Synthesis of Para-Bridged Bipyridine Bis-Cyanomethyl Analogues

Benzyl (compound 14), allyl (compound 15), propargyl (compound 16), coumarin (compound 17), acetal (compound 18), and carboxylate (compound 19) analogues of para-bridged bis-CN viologen were synthesized according to Scheme 4:

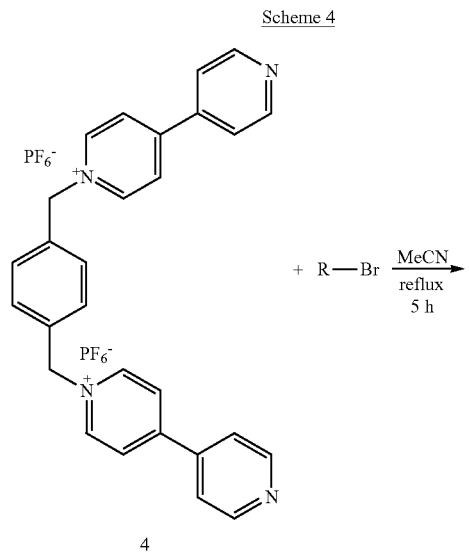

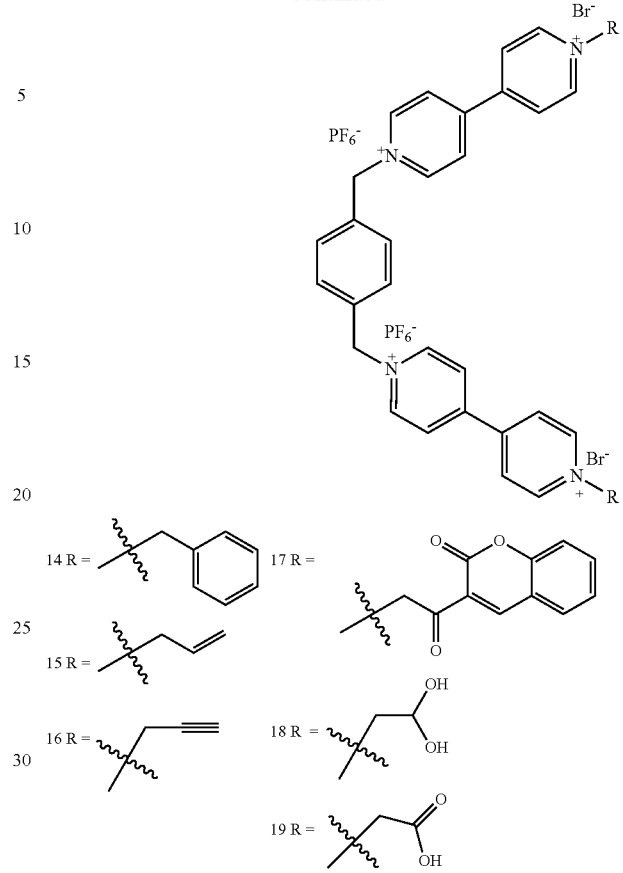

1',1''-(1,4-phenylenebis(methylene))bis(1-(benzyl)-4,4'-bipyridine-1,1'-diium)bromide, 14

Bromo benzyl (2.78 g, 16.28 mmol) was dissolved in 10 mL of acetonitrile, and the solution was brought to reflux. The hexafluorophosphate salt of compound 4 (1 g, 1.42 mmol) was dissolved in 50 mL of acetonitrile and added within 1 h to the bromo benzyl refluxing solution. After the addition was completed, the mixture was refluxed additional 3 h. The mixture was allowed to cool down to room temperature. The yellow precipitate was filtered and washed with cold acetonitrile, then dried under vacuum. Yield: 0.59 g, 46%. $^1$H NMR (D$_2$O, 400 MHz): δ (ppm) 9.20-9.23 (8H, m), 8.57-8.61 (8H, m), 7.68 (4H, s), 7.59 (8H, s), 6.04 (4H, s), 5.99 (4H, s). $^{13}$C NMR (D$_2$O, 100 MHz): δ (ppm) 153.31, 153.06, 148.50, 148.37, 136.93, 135.05, 133.21, 133.02, 132.53, 132.16, 130.16, 130.13, 129.99, 67.70, 67.00.

1',1''-(1,4-phenylenebis(methylene))bis(1-allyl-4,4'-bipyridine-1,1'-diium)bromide, 15

Compound 15 was synthesized as described above for compound 14, reflux time 3 h. Allyl bromide (1.97 g, 16.28 mmol), compound 4 (1.0 g, 1.42 mmol). The target compound was isolated as a bright yellow solid. Yield: 0.48 g, 42%. $^1$H NMR (D$_2$O, 400 MHz): δ (ppm) 9.21-9.23 (4H, d), 9.14-9.16 (4H, d), 8.601 (8H, m), 7.68 (4H, s), 6.19-6.26 (2H, m), 6.03 (4H, s), 5.57-5.67 (2H, quad), 5.37-5.39 (2H, d). $^{13}$C NMR (D$_2$O, 100 MHz): δ (ppm) 153.48, 153.04, 148.70, 148.66, 148.65, 148.63, 148.52, 148.46, 148.38, 136.95, 133.21, 132.33, 130.13, 129.89, 126.60, 67.01, 66.54.

1',1''-(1,4-phenylenebis(methylene))bis(1-propargyl-1-4,4'-bipyridine-1,1'-diium)bromide 16

Compound 16 was synthesized as described above for compound 14, reflux time 3 h. Propargyl bromide (2.42 g, 16.28 mmol), compound 4 (1.0 g, 1.42 mmol). The target compound was isolated as a brown solid. Yield: 0.48 g, 42%. $^1$H NMR (D$_2$O, 400 MHz): δ (ppm) 9.18-9.24 (8H, m), 8.57-8.66 (8H, m), 7.26 (8H, s), 6.02 (8H, s).

1',1''-(1,4-phenylenebis(methylene))bis(1-(2-oxo-2-(2-oxo-2H-chromen-3-yl)ethyl)-4,4'-bipyridine-1,1'-diium)bromide, 17

Compound 17 was synthesized as described above for compound 14, reflux time 3 h. Bromo acetyl coumarin (2.17 g, 8.14 mmol), compound 4 (0.5 g, 0.707 mmol). The target compound was isolated as a blue-green solid. Yield: 0.42 g, 54%. $^1$H NMR (D$_2$O, 400 MHz): δ (ppm) 9.22-9.24 (4H, d), 9.03-9.05 (4H, d), 8.98 (2H, s), 8.62-8.65 (8H, m), 7.87-7.92 (4H, m), 7.68 (4H, s), 7.51-7.54 (4H, m), 6.03 (4H, s). $^{13}$C NMR (D$_2$O, 100 MHz): δ (ppm) 191.42, 164,08, 158.17, 155.17, 155.15, 153.80, 153.47, 150.00, 149.94, 148.72, 148.66, 139.61, 139.58, 137.12, 134.38, 133.39, 133.34, 130.32, 129.77, 128.83, 123.18, 121.00, 119.62, 112.48, 109.52, 67.17.

1',1''-(1,4-phenylenebis(methylene))bis(1-(2,2-dihydroxyethyl)-4,4'-bipyridine-1,1'-diium)bromide, 18

Compound 18 was synthesized as described above for compound 14, reflux time 5 h. Bromo acetyl acetaldehyde (3.21 g, 16.28 mmol), compound 4 (1.0 g, 1.42 mmol). The target compound was isolated as a dark green solid. Yield: 0.30 g, 22%. $^1$H NMR (D$_2$O, 400 MHz): δ (ppm) 9.19-9.21 (4H, d), 9.09-9.11 (4H, d), 8.56-8.62 (8H, m), 7.64-7.66 (8H, m), 5.95 (4H, s), 5.6 (4H, s). $^{13}$C NMR (D$_2$O, 100 MHz): δ (ppm) 153.53, 153.40, 151.38, 151.36, 149.67, 148.78, 148.62, 148.06137.05, 133.32, 133.27, 133.16, 130.53, 130.40, 130.36, 130.31, 130.26, 129.52, 129.49, 126.31, 89.76, 68.60, 67.17.

1',1''-(1,4-phenylenebis(methylene))bis(1-(carboxymethyl)-4,4'-bipyridine-1,1'-diium)bromide, 19

Compound 19 was synthesized as described above for compound 14, reflux time 12 h. Bromo acetic acid (2.26 g, 16.28 mmol), compound 4 (1.0 g, 1.42 mmol). Yield: 0.30 g, 22%. $^1$H NMR (D$_2$O, 400 MHz): δ (ppm) 9.20-9.22 (4H, d), 9.07-9.09 (4H, d), 8.59-8.61 (4H, d), 8.54-8.56 (4H, d), 7.67 (8H, s), 6.02 (4H, s), 4.53 (4H, s). $^{13}$C NMR (D$_2$O, 100 MHz): δ (ppm) 153.34, 152.31, 149.04, 148.34, 136.80, 133.07, 130.02, 129.95, 129.43, 66.84, 57.052.

The analogues were screened for reaction with 1 mM solutions of homocysteine, cysteine, and glutathione in 83.3 mM TRIS buffer, pH 7.0, at room temperature. The reactions were evaluated after 1 minute and 10 minutes. The final concentration of the analogues in the solutions ranged from 6-8 mM. The concentration of each analogue is shown below in Table 3.

TABLE 3

| Analogue | Concentration (mM) |
|---|---|
| 14 - benzyl | 7.26 |
| 15 - allyl | 8.15 |
| 16 - propargyl | 8.19 |

TABLE 3-continued

| Analogue | Concentration (mM) |
|---|---|
| 17 - coumarin | 6.00 |
| 18 - acetal | 7.28 |
| 19 - carboxylate | 7.80 |

Figure 18:
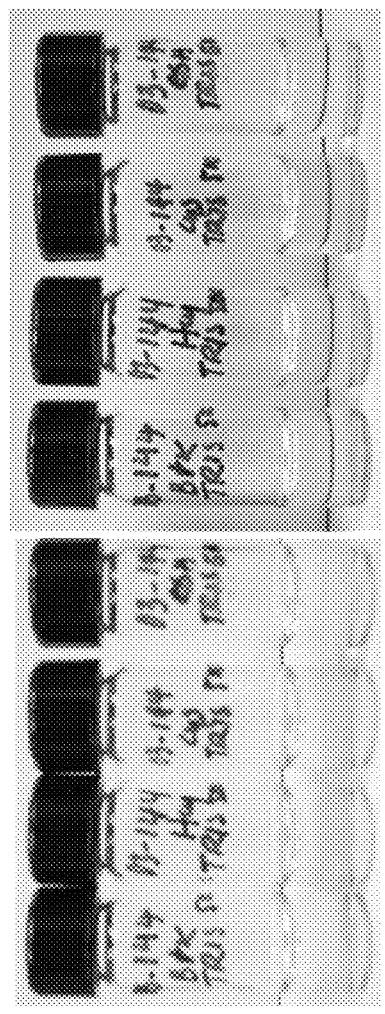
FIG. 18 is a photograph showing the reaction of the para-bridged bis-carboxylate viologen with a blank, homocysteine, cysteine, and glutathione after 1 minute and 10 minutes at room temperature.
Figure 19:
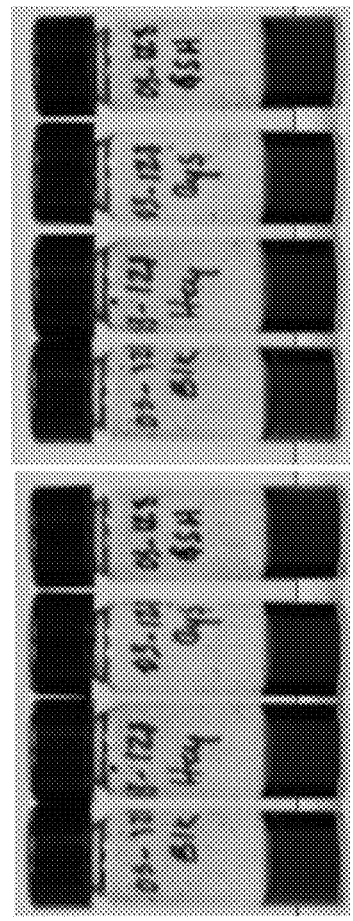
FIG. 19 is a photograph showing the reaction of the para-bridged bis-propargyl viologen with a blank, homocysteine, cysteine, and glutathione after 1 minute and 10 minutes at room temperature.
Figure 20:
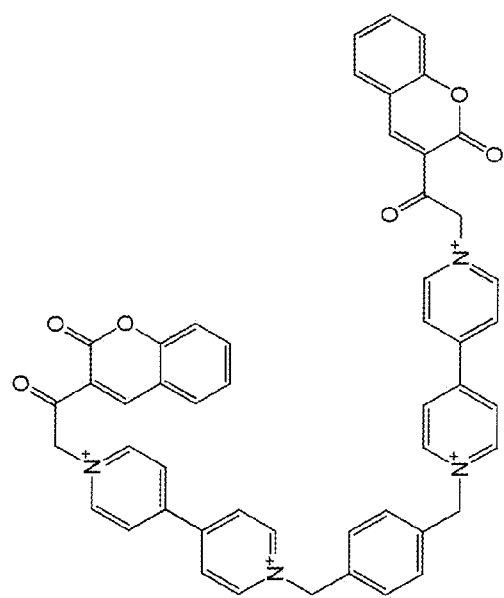
FIG. 20 is a photograph showing the reaction of the para-bridged bis-coumarin viologen with a blank, homocysteine, cysteine, and glutathione after 1 minute and 10 minutes at room temperature.
Figure 20:
Figure 21:
FIG. 21 is a photograph showing the reaction of the para-bridged bis-acetal viologen with a blank, homocysteine, cysteine, and glutathione after 10 minutes at room temperature.
Figure 21:
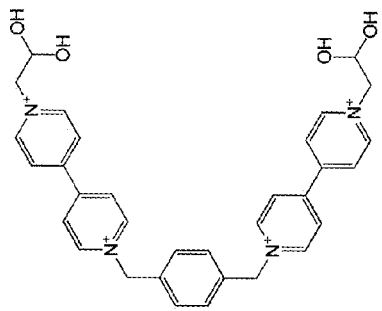

The benzyl, allyl, and carboxylated analogues did not react with any of the thiols at room temperature. FIG. 18 shows the results of the carboxylate analogue reaction. The propargyl, coumarin, and acetal analogues produced dark solutions when mixed with the thiols (FIGS. 19-21, respectively). The propargyl analogue produced a dark brown solution. The coumarin analogue produced a dark purple solution and formed a precipitate. The acetal analogue produced a dark green solution.

The benzyl and allyl analogues were further investigated in 83.3 mM TRIS buffer (pH 7.0) under reflux conditions (FIGS. 22 and 23, respectively). The benzyl analogue reacted selectively with 1 mM Hcy, producing a blue color after 5 minutes. No reaction was seen with 1 mM Cys or 1 mM GSH. After 5 minutes of reflux, the allyl analogue produced solutions of different color, depending on the thiol used.

Example 3

Reactions of Compound 5 with Thiols and Amino Acids

Figure 24:
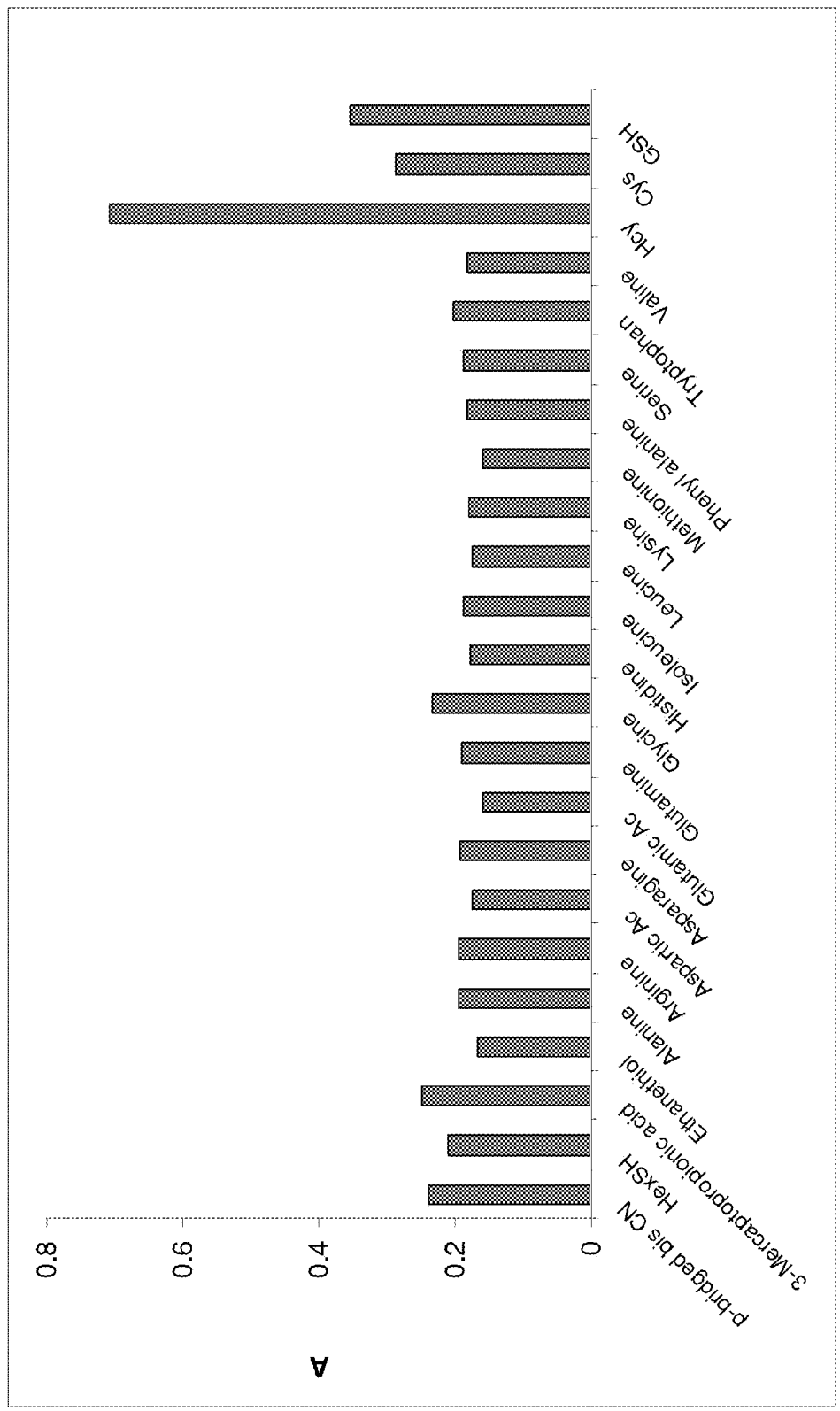
FIG. 24 is a bar graph depicting the absorbance (at 534 nm) produced by the reaction of para-bridged bis-CN viologen with various thiols and amino acids.

The reactions of compound 5, (1',1''-(1,4-phenylenebis(methylene))bis(1-(cyanomethyl)-4,4'-bipyridine,1,1'-diium)bromide), with biological thiols (Hcy, Cys, and GSH), other thiols (e.g., ethanethiol, hexanethiol, and 3-mercaptopropionic acid), and amino acids were studied. Compound 5, 8 mM, was mixed with 1 mM thiol or amino acid in 83.3 mM TRIS buffer (pH 7.0) and allowed to react for 30 minutes. The absorbance at 534 nm was then measured. As shown in FIG. 24, only Hcy showed a significant increase in absorbance, thereby demonstrating the specificity of compound 5 for Hcy detection.

Example 4

Investigation of Reaction Mechanism 4.1 Electrochemical Titration

Because of the redox properties that these type of compounds exhibit, a possible redox type mechanism was investigated by electrochemical titration of compound 5 with Hcy, Cys, GSH and 3-mercaptopropionic acid (MPA). MPA has been used as a control mimicking the thiol moiety of Hcy.

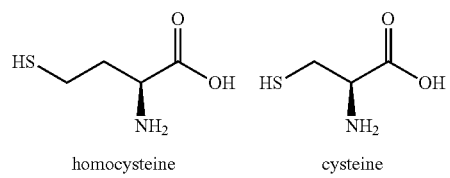

homocysteine          cysteine

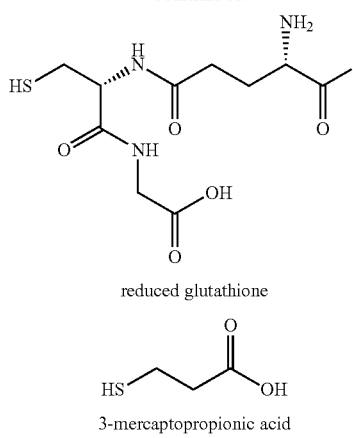

reduced glutathione

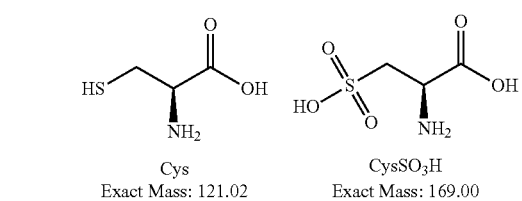

Cys
Exact Mass: 121.02

CysSO₃H
Exact Mass: 169.00

Figure 26:
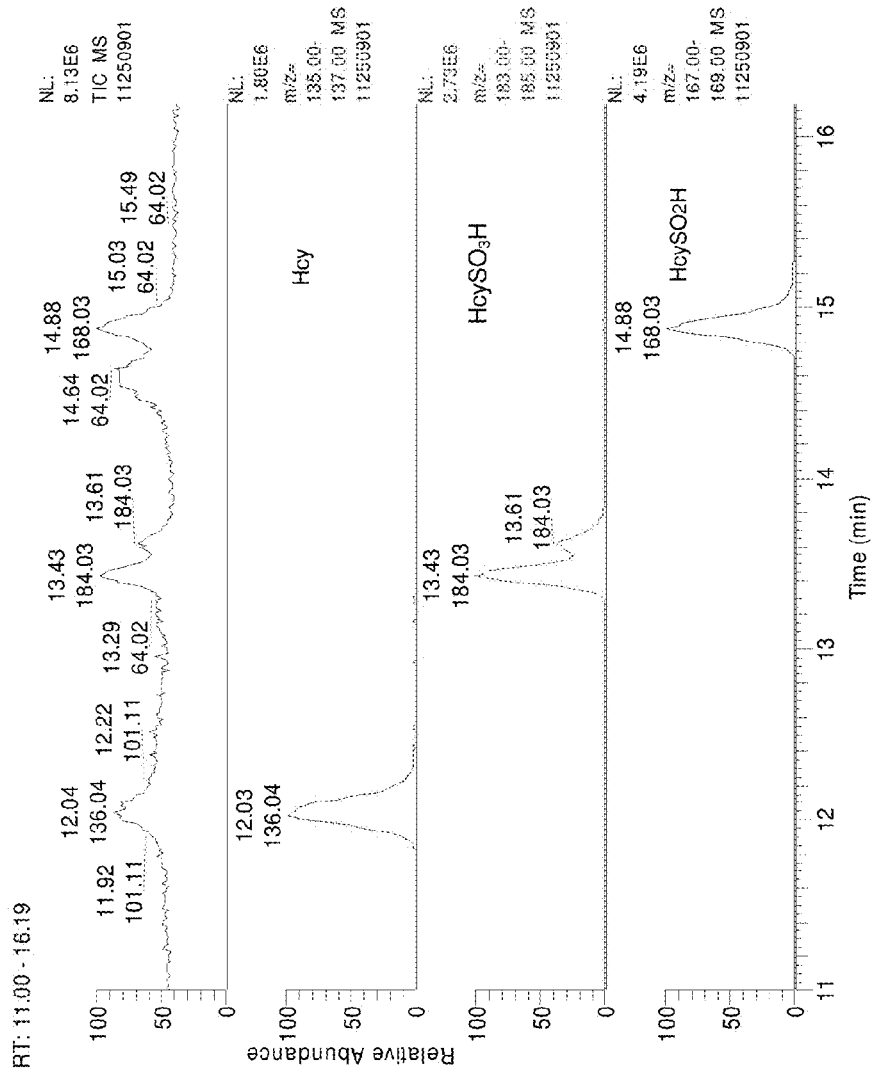
FIG. 26 is a series of LC/MS traces of homocysteine, homocysteine sulfonic acid, and homocysteine sulfinic acid. The top trace is total ion count.

FIG. 26 shows the LC/MS traces for control sample mixtures containing Hcy and its oxidation products: homocysteine sulfonic acid (HcySO₃H) and homocysteine sulfinic acid (HcySO₂H).

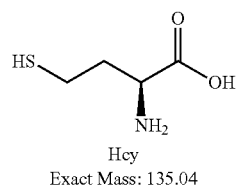

Hcy
Exact Mass: 135.04

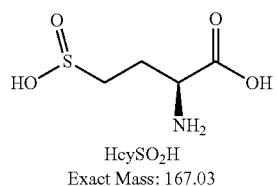

HcySO₂H
Exact Mass: 167.03

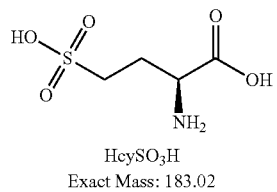

HcySO₃H
Exact Mass: 183.02

3-mercaptopropionic acid

Electrochemical titration was carried out at room temperature and under inert (i.e., argon) atmosphere. Cyclic voltammograms were obtained at 20 mV/s 20 minutes after the addition of 0.5, 1, 2, 5, and 10 equivalents of the corresponding thiol to compound 5 (8 mM in 10 mM phosphate buffer, pH 7.0). The working electrode was glass, the reference electrode was SCE, and the counter electrode was Pt. As shown in Table 4, changes in both the cathodic and anodic current were observed for Hcy, Cys, and 3-MPA when only 0.5 equivalents of the thiol were added to compound 5; these changes remained constant after the addition of 10 equivalents. Titration with GSH, showed a different behavior, small changes in both the anodic and cathodic current were observed. However, when 5 equivalents were added, a decrease in the anodic current was observed.

TABLE 4

| Thiol | Δ Eox 1 | Δ Eox 2 | Δ Ered 1 | Δ Ered 2 |
|---|---|---|---|---|
| 3-MPA | 0.06 | 0.06 | 0.06 | 0.07 |
| Cys | 0.13 | 0.05 | 0.02 | 0.17 |
| Hcy | 0.15 | 0.04 | 0.04 | 0.17 |
| GSH | 0.06 | 0 | 0 | 0.14* |

*This change in current was observed only after 5 equivalents were added to the viologen solution.

4.2 Identification of Reaction Products

To corroborate a possible redox mechanism, the products from the reaction between compound 5 and thiols are being investigated by LC/MS. A LC/MS method has been developed to identify possible oxidation products from Hcy, Cys, and GSH. Sample mixtures containing a thiol or an oxidation product at a concentration of 50 µM were evaluated by LC/MS. The solvent system was methyl cyanide (MeCN): H₂O:100 mM ammonium acetate pH 5, 5:4:1. The flow rate was 0.2 mL/minute, with an injected volume of 10 µL. The LC/MS detector was operated in positive mode.

Figure 25:
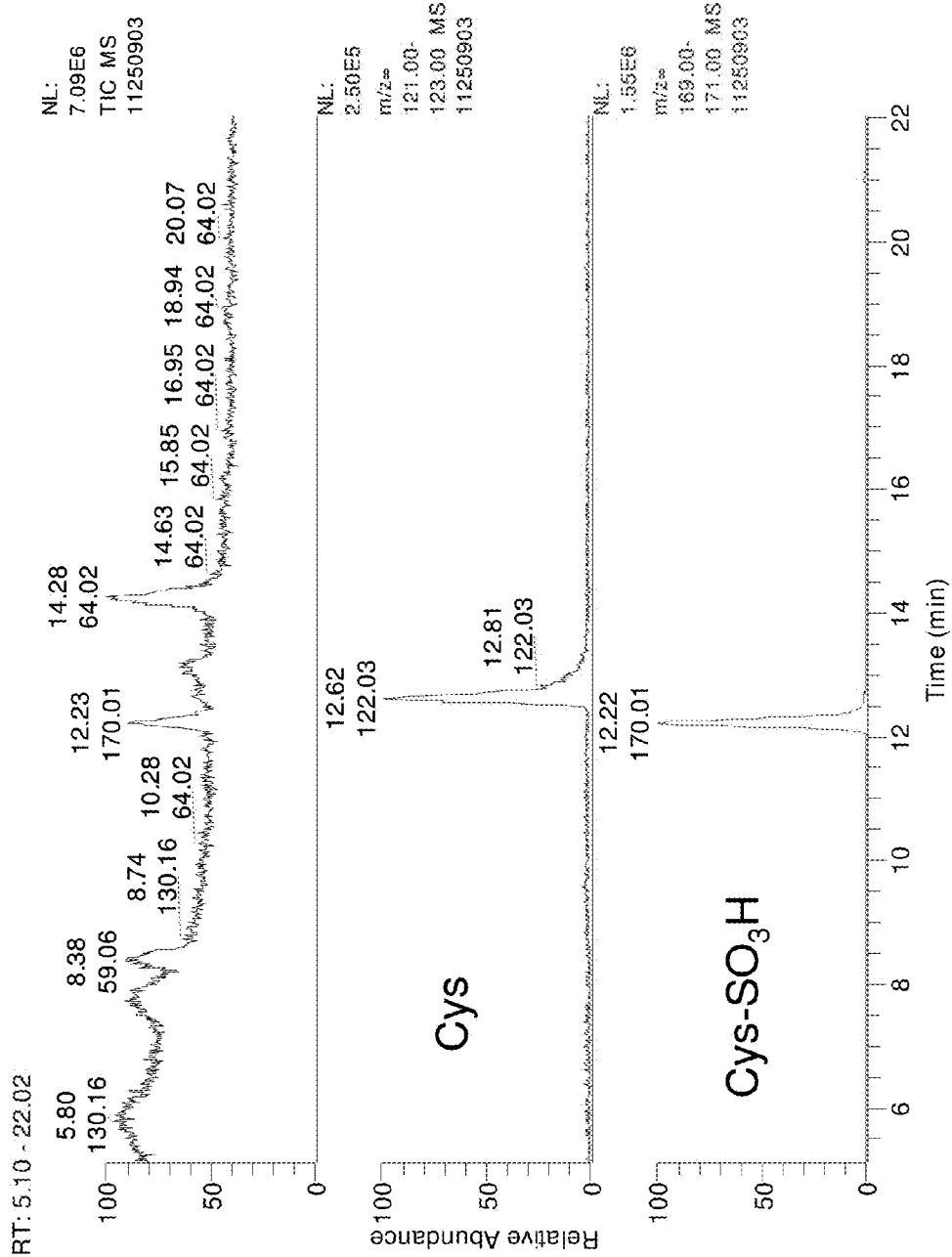
FIG. 25 is a series of LC/MS traces of cysteine and cysteine sulfonic acid. The top trace is total ion count.

FIG. 25 shows the LC/MS traces for control sample mixtures containing Cys or its oxidation product, cysteine sulfonic acid (CysSO3H), at a concentration of 50 µM.

Figure 27:
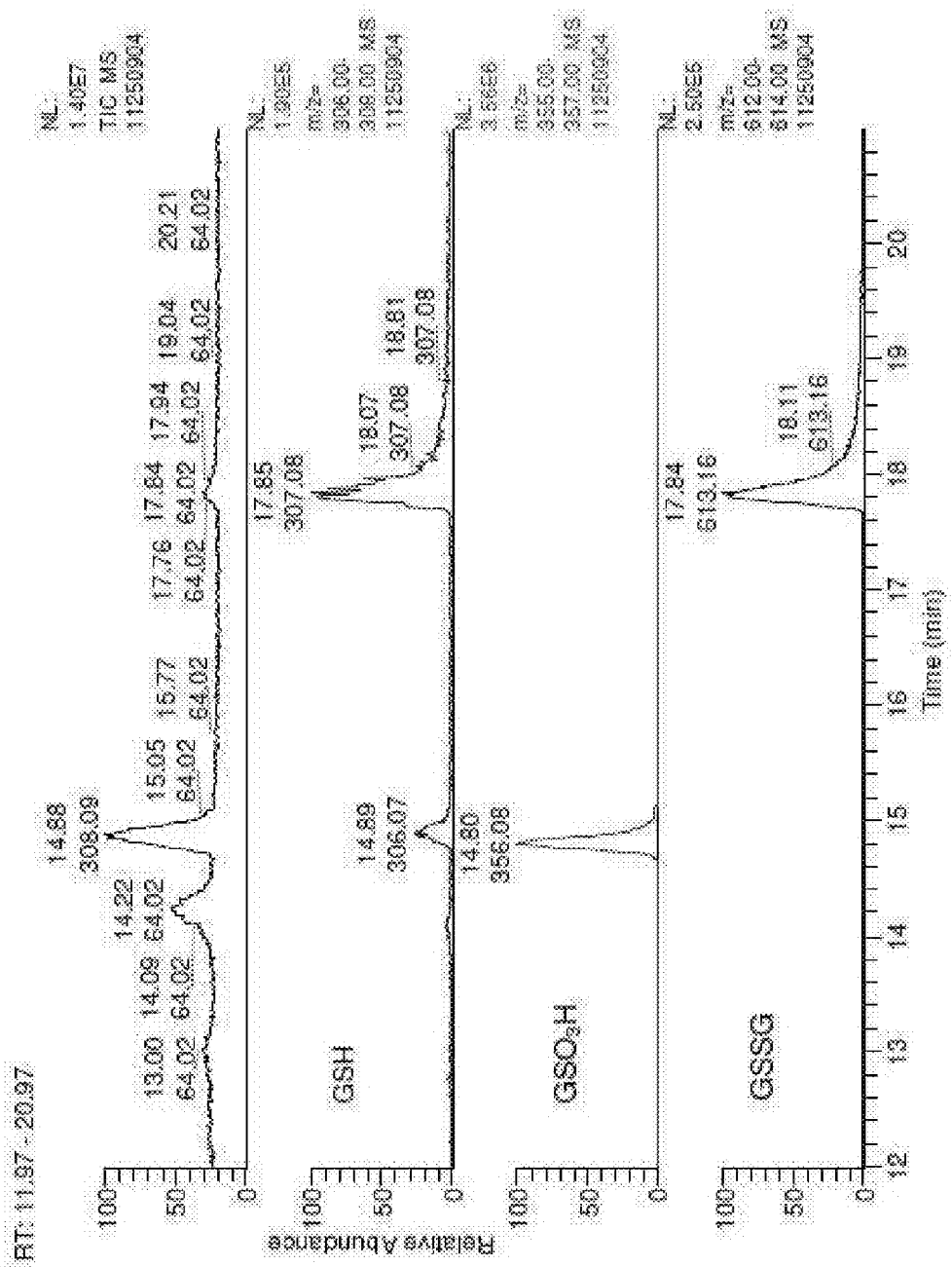
FIG. 27 is a series of LC/MS traces of glutathione, glutathione sulfonic acid, and glutathione disulfide. The top trace is total ion count.

FIG. 27 shows the LC/MS traces for control sample mixtures containing glutathione and its oxidation products: glutathione sulfonic acid (GSO₃H) and glutathione disulfide (GSSG).

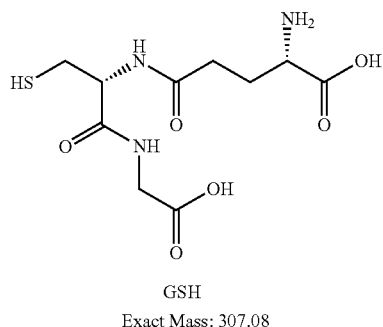

GSH
Exact Mass: 307.08

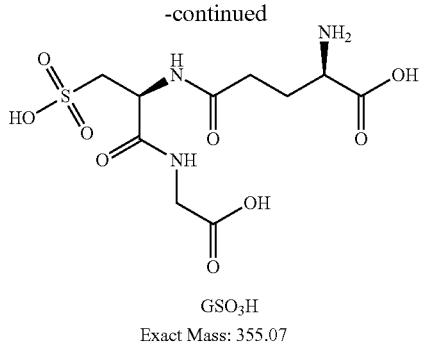

GSO₃H
Exact Mass: 355.07

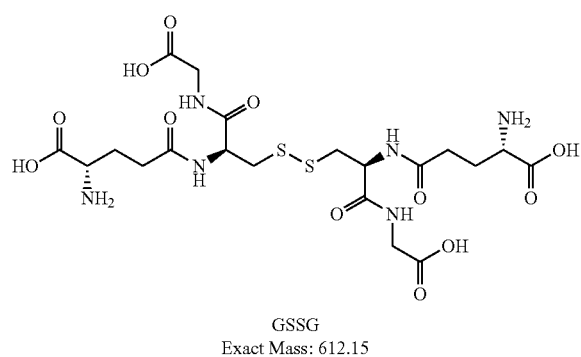

GSSG
Exact Mass: 612.15

Example 5

Reactions of Compound 17 with Thiols

Based on the preliminary results from the colorimetric and electrochemical titration carried out for the reaction of compound 5 with thiols, the use of compound 17 (1',1''-(1,4-phenylenebis(methylene))bis(1-(2-oxo-2-(2-oxo-2H-chromen-3-yl)ethyl)-4,4'-bipyridine-1,1'-diium)bromide) for GSH detection was further investigated. It is hypothesized that a supramolecular assembly type mechanism may be involved in the color changes observed between the reaction of GSH and the disclosed viologen analogues. Since compound 17 contains a fluorophore, it was envisioned that a fluorescence detection method might be advantageous as increased sensitivity typically is obtained with fluorescence-based methods.

As demonstrated in Example 2, initial results for the reaction of compound 17 at a 6 mM concentration with thiols (Hcy, Cys, GSH) showed no visible selectivity. At a 6 mM concentration of compound 17, deep purple solutions and formation of a dark precipitate were observed for each thiol. However, when the concentration of compound 17 was reduced to 1 mM in 500 mM TRIS buffer pH 7.0, a deep purple solution was obtained within 5 minutes upon reaction with Hcy and Cys at room temperature, and a pale pink solution was obtained upon reaction with GSH.

Energy-minimized structures of the single bridged ortho-, meta- and para-bis coumarin viologen analogues are shown in FIG. 28. Pi-pi stacking of the coumarin moieties is observed in all three analogues, but only the para-bridged analogue can fit GSH inside the cavity as shown in FIG. 29. It is anticipated that the binding of the GSH to the para-bis coumarin viologen (compound 17) will disrupt the π-π stacking, and turn "on" the fluorescence of the compound via a charge transfer mechanism.

Screening of the reaction of compound 17 with Hcy, Cys, and GSH by fluorescence is currently underway. To complete this series of single-bridged viologen analogues, the meta- and ortho-isomers are currently being synthesized, using a similar methodology to that previously described in Example 2.

Example 6

Synthesis of Single Bridged Para-Bis Rhodol Viologen

Mono(1',1''-(1,4-phenylenebis(methylene))bis(1-(3-(2-(10-(dimethylimino)-1-hydroxy-10H-benzo[c]xanthen-7-yl)benzoyloxy)propyl)-4,4'-bipyridine-1,1'-diium))tetrabromide, 21

The use of near-infrared dyes to produce both symmetric and asymmetric single bridged viologens for GSH detection is currently underway. Compound 21 a single bridged para-viologen bis-rhodol analogue may be synthesized as shown in Scheme 5:

Scheme 5

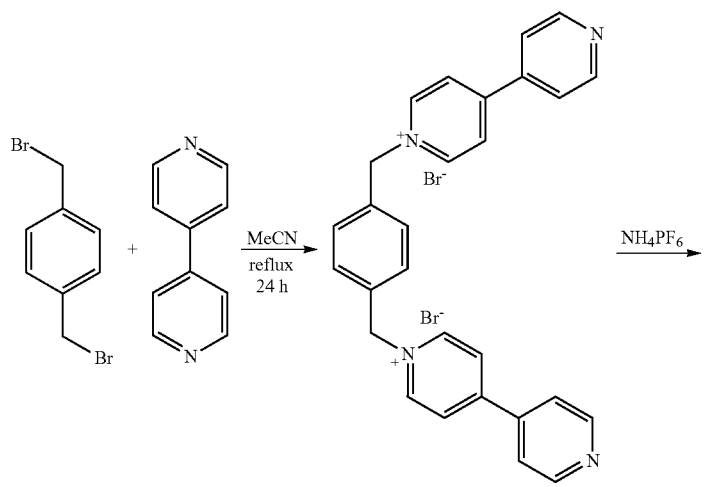

-continued
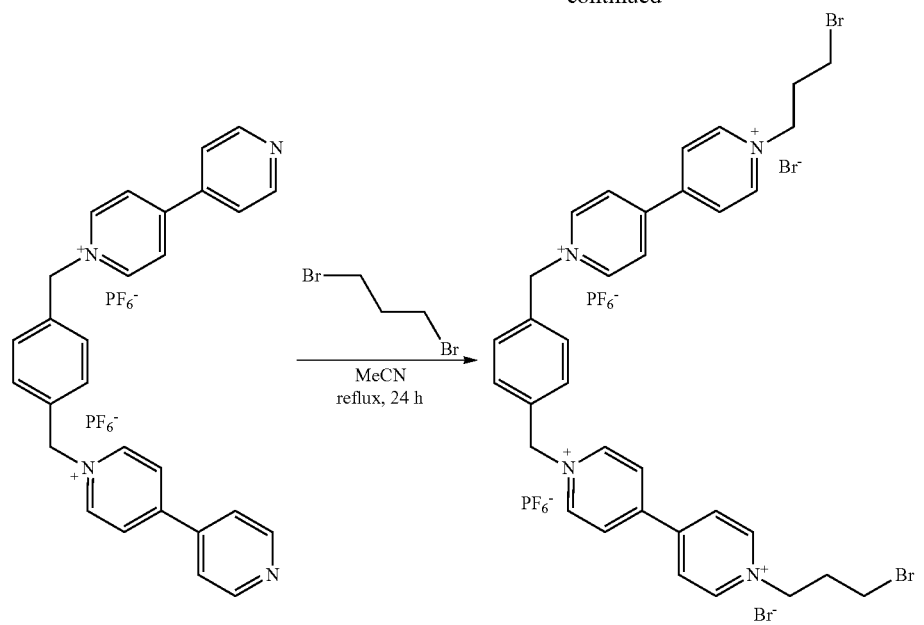
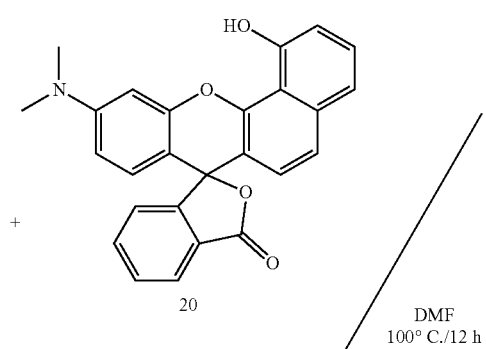
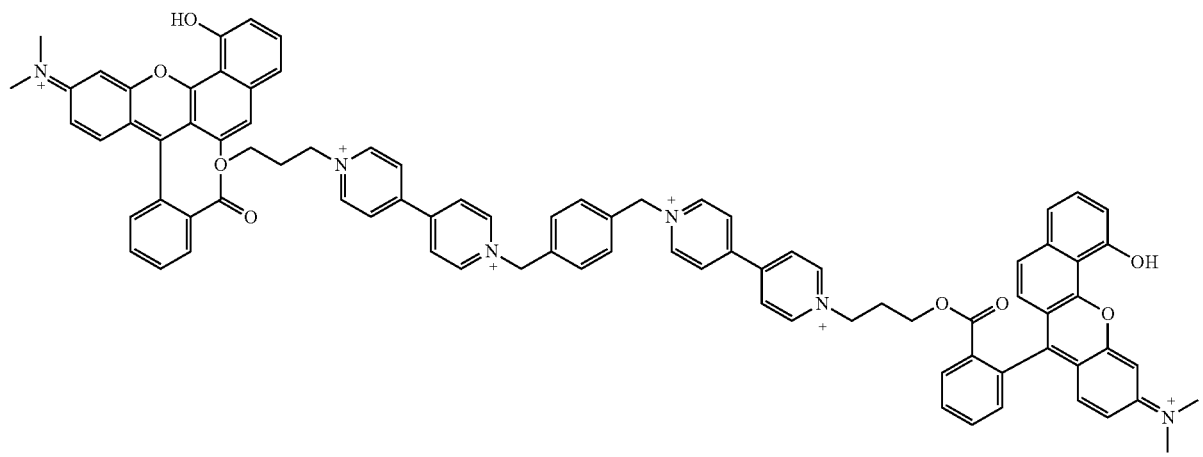

Rhodol 20, has been synthesized (Scheme 6) according to published protocols. (Strongin et al., "Developing Fluorogenic Reagents for Detecting and Enhancing Bloody Fingerprints," NCJ 227841, Grant Report, 2009.)

Scheme 6

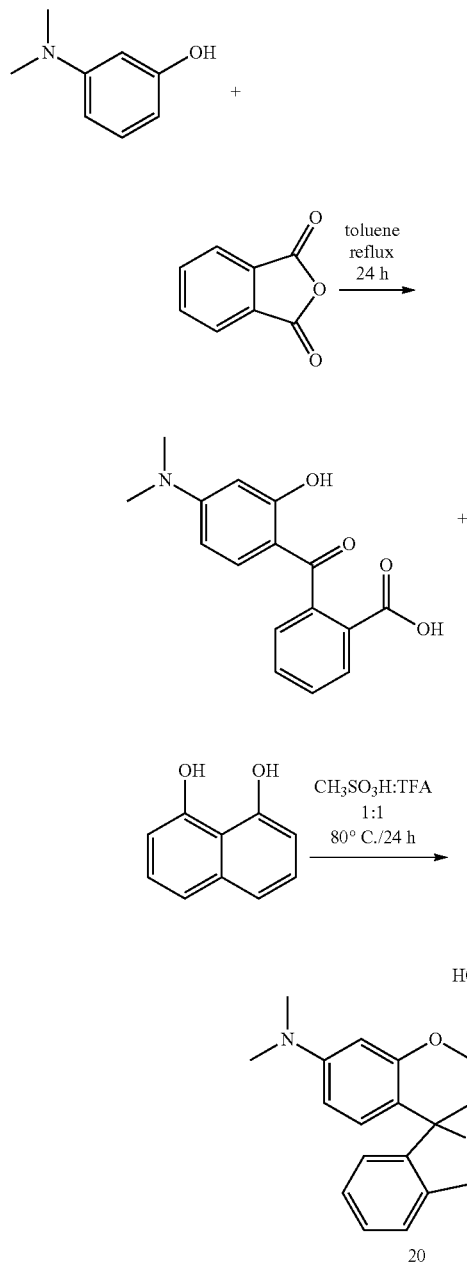

Figure 30:
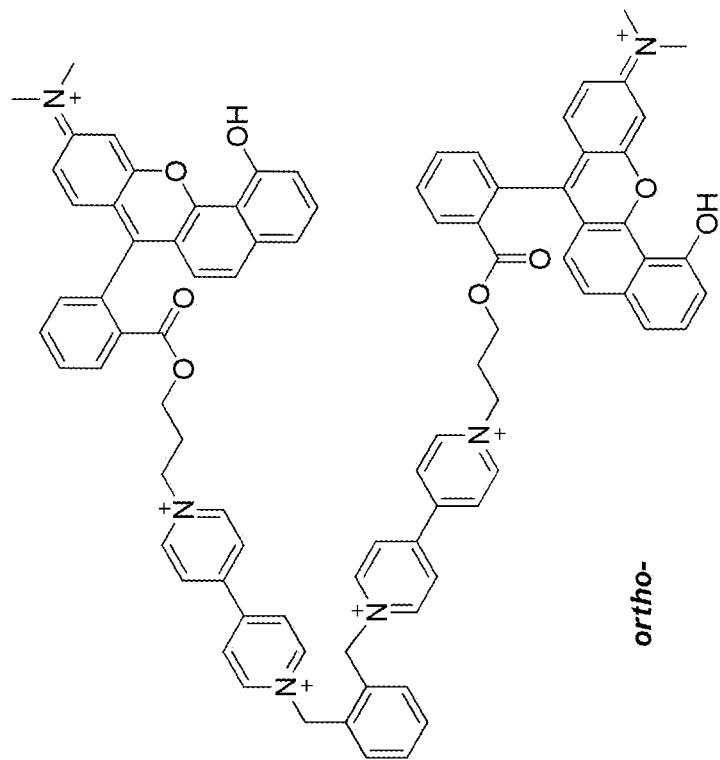
FIGS. 30-32 show the energy-minimized structures of single bridged ortho-, meta- and para-bis rhodol viologen analogues, respectively.
Figure 30:
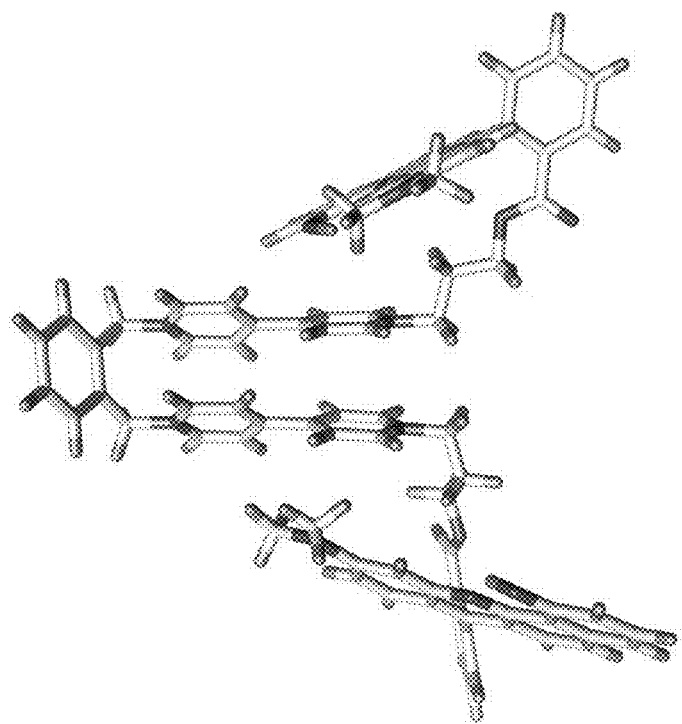
Figure 31:
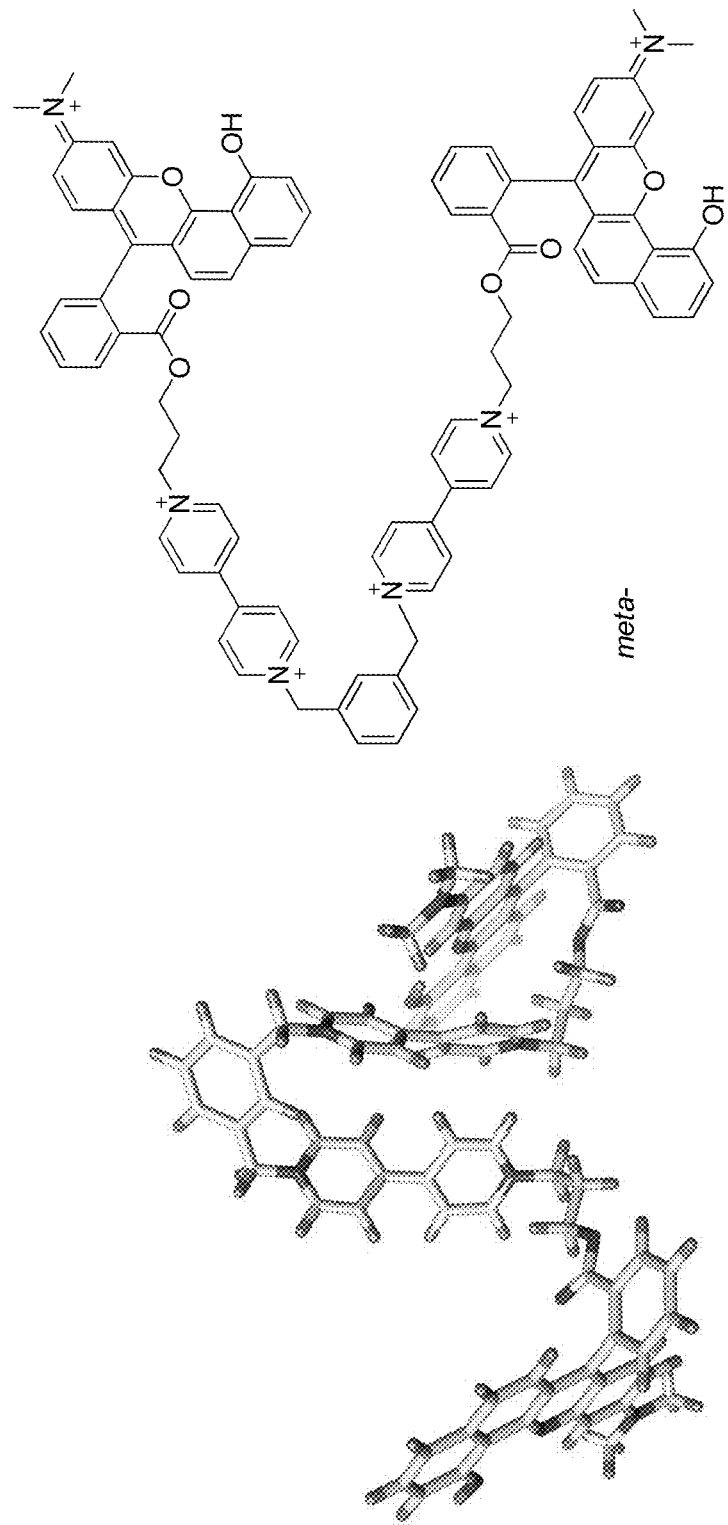
Figure 32:
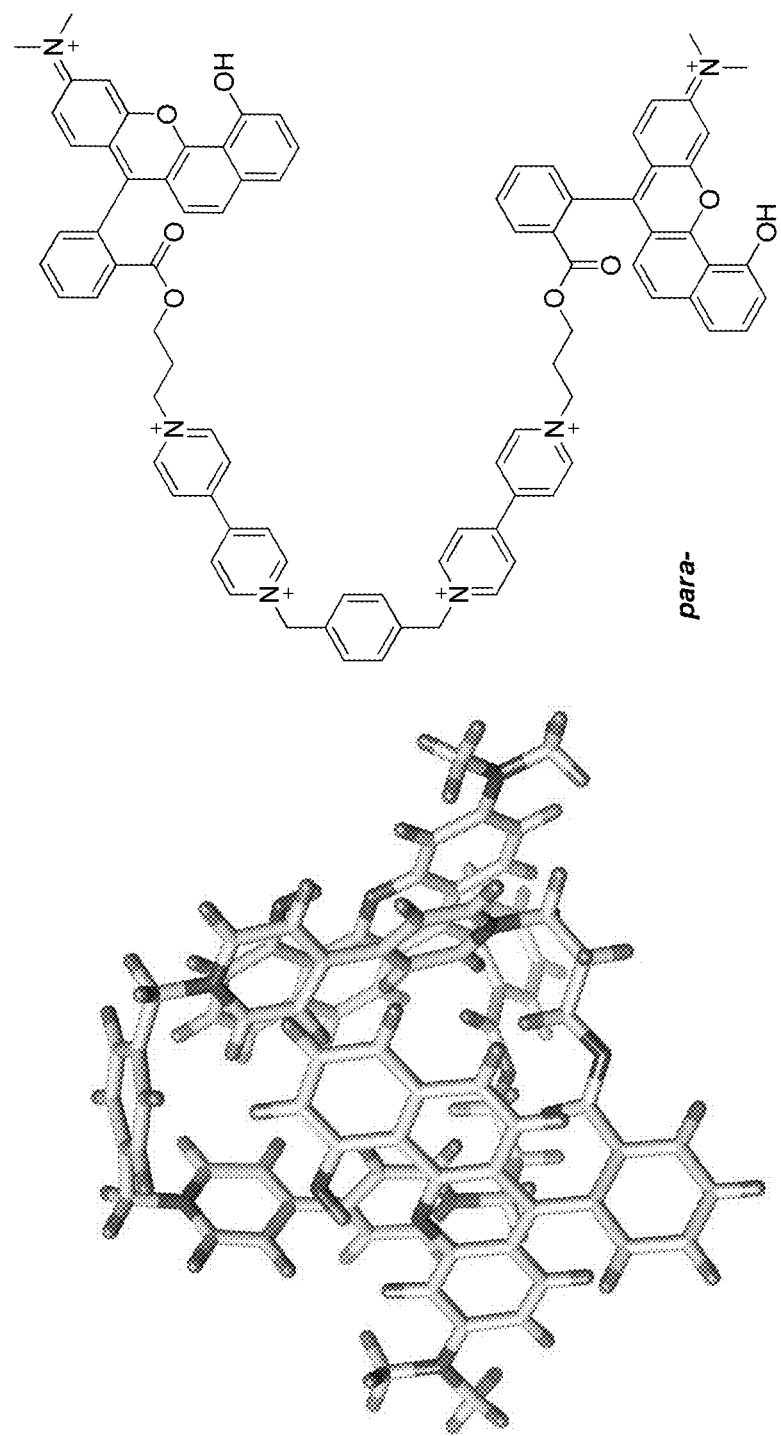

Energy-minimized structures for each of the bis-rhodol viologen isomers are shown in FIGS. 30-32.

Example 7

Screening of Para-Bridged bis-CN Viologen in Deproteinized Bovine Plasma

Figure 33:
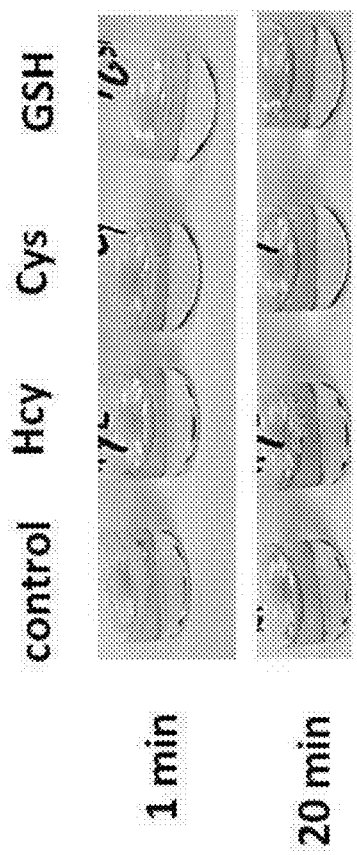
FIG. 33 is a photograph showing the reaction of the para-bridged bis-CN viologen with a blank, homocysteine, cysteine, and glutathione in deproteinized bovine plasma.

Plasma proteins from bovine plasma were removed by precipitation with MeCN. The lyophilized filtrate was reconstituted with water and used to screen the performance of the para-bridged bis-CN viologen (1',1"-(1,4-phenylenebis(methylene))bis(1-(cyanomethyl)-4,4'-bipyridine-1,1'-diium) bromide) for thiol, detection at room temperature. Diluted deproteinized plasma (35.7%) was spiked with thiols (Hcy, Cys and GSH) at a 714 μM final concentration in 7.14 mM phosphate buffer. As shown in FIG. 33, selectivity for Hcy over Cys and GSH was observed after 20 min. These results correlate with those observed in control buffered thiol solutions.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having:

(a) Formula I

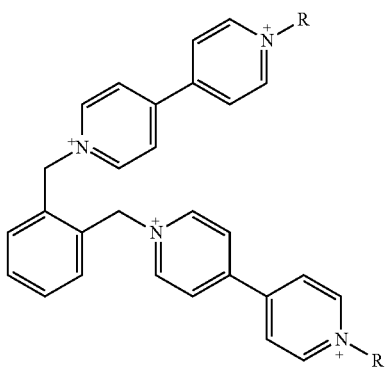

where R is a lower alkyl nitrile, alkynyl, 2-oxo-2-(2-oxo-2H-chromen-3-yl)ethyl, 2,2-dihydroxyethyl, carboxymethyl, or a fluorophore; or (b) Formula II

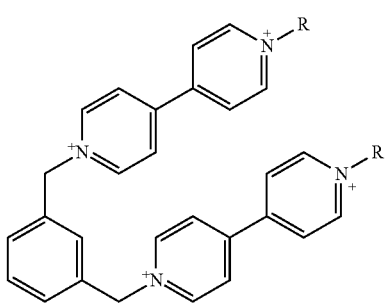

where R is a lower alkyl nitrile, alkenyl, alkynyl, 2-oxo-2-(2-oxo-2H-chromen-3-yl)ethyl, 2,2-dihydroxyethyl, carboxymethyl, or a fluorophore; or (c) Formula III

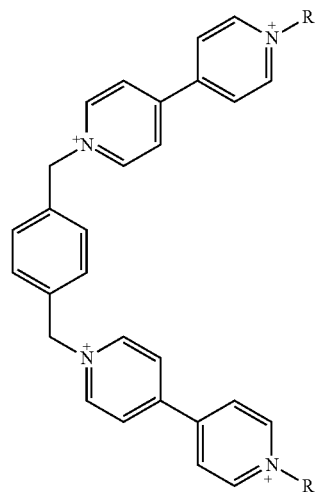

where R is a lower alkyl nitrile, alkenyl, alkynyl, 2-oxo-2-(2-oxo-2H-chromen-3-yl)ethyl, 2,2-dihydroxyethyl, carboxymethyl, or a fluorophore, wherein the fluorophore has the structure:

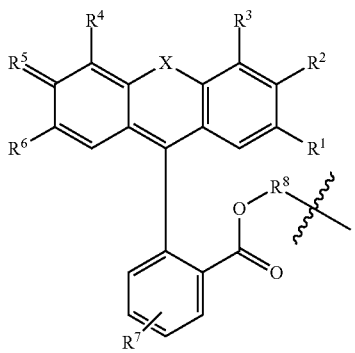

where X is oxygen, sulfur, CH$_2$ or NH; R$^1$, R$^2$, R$^3$, R$^4$, and R$^6$ independently are —H, —OH, lower alkyl, carboxyalkyl, amino, substituted amino, alkoxy, or halogen, or R$^2$ and R$^3$ together may form a substituted or unsubstituted cycloalkyl or aryl; R$^5$ is oxygen, imino, substituted alkyl imino, or substituted or unsubstituted cycloalkyl imino; R$^7$ is —H, alkyl, acyl, carboxyl, nitro, amino, substituted amino; and R$^8$ is absent or alkyl.

2. The compound of claim 1 according to Formula I where R is

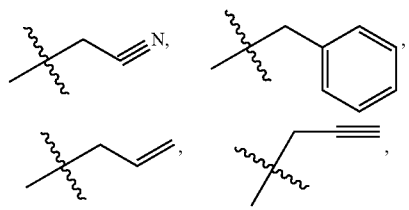

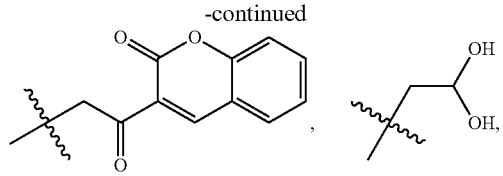

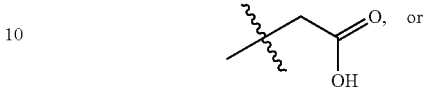

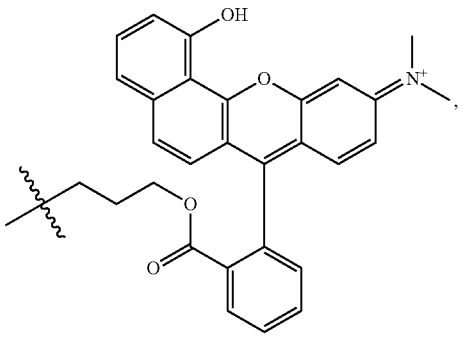

or according to Formula II where R is

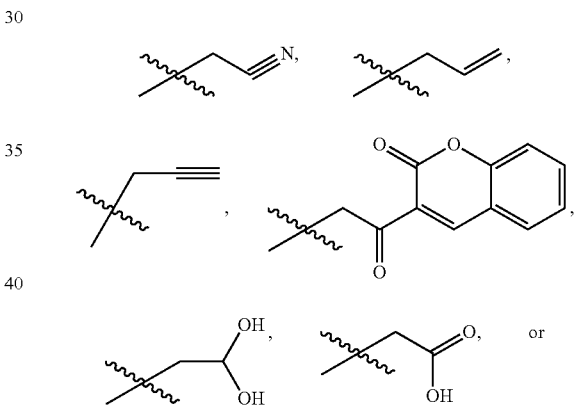

or according to Formula III where R is

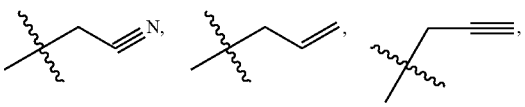

-continued

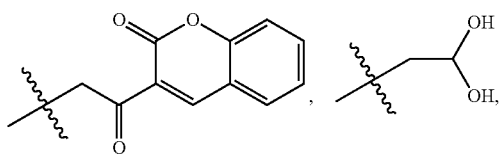

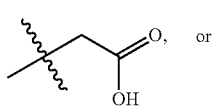

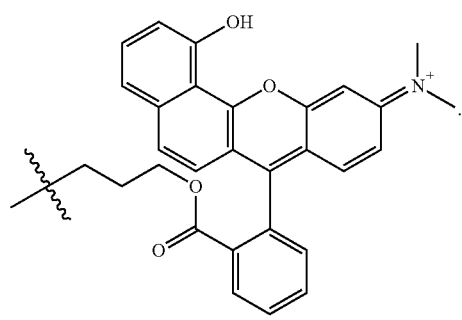

3. The compound according to claim 1, where the compound is:

-continued

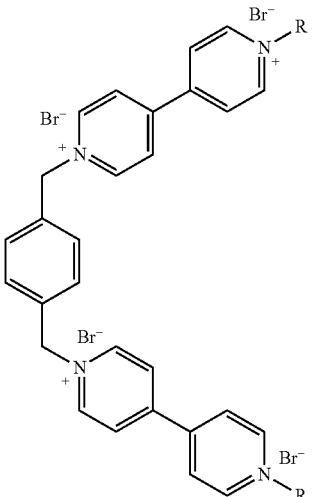

where R is:

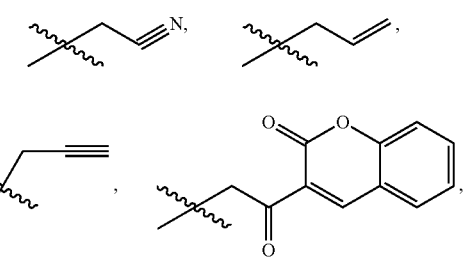

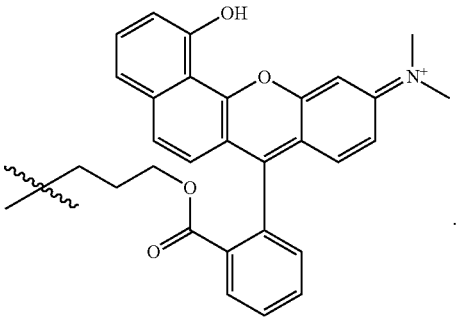

4. A method for detecting a thiol, comprising:
   forming a solution by combining a sample comprising a thiol with a compound according to claim 1;
   allowing a reaction between the thiol and the compound according to claim 1 in the solution to proceed for an effective period of time to a produce a detectable change in the solution's absorbance spectrum, emission spectrum, or both, where the change indicates that the thiol is present; and
   detecting the change.

5. The method of claim 4, where the thiol is cysteine, homocysteine, glutathione, or a combination thereof.

6. The method of claim 4, where the compound according to claim 1 is:

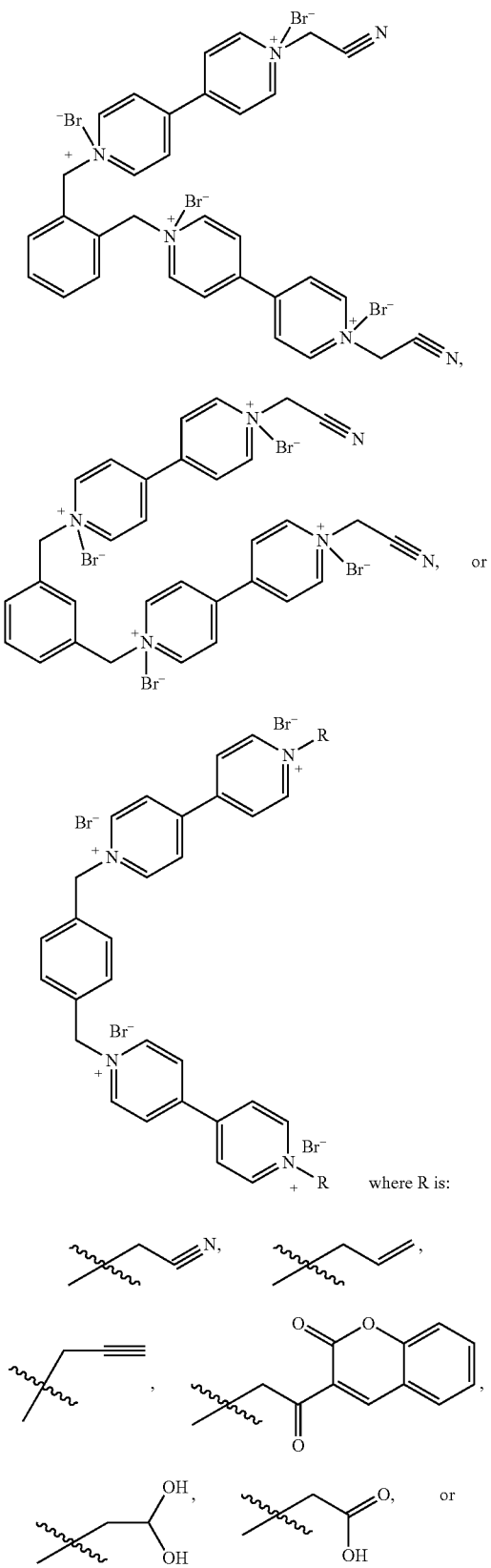

7. The method of claim 4, where the effective period of time is 1-60 minutes.

8. The method of claim 4, where the solution further comprises a buffer selected from HEPES (N'-2-hydroxyethylpiperazine-N'-2-ethanesulfonic acid), MOPS (3-(N-morpholino)propanesulfonic acid), phosphate, and TRIS (tris (hydroxymethyl)-aminomethane) buffers.

9. The method of claim 4, where the thiol is homocysteine, glutathione, or a combination thereof, the buffer is a phosphate or TRIS buffer, and the compound according to claim 1 is:

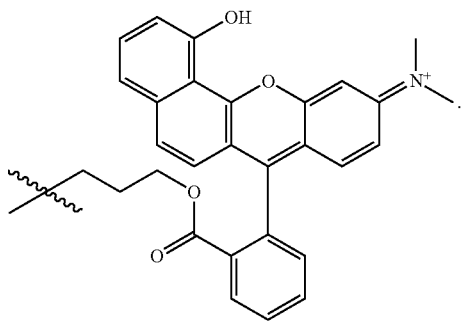

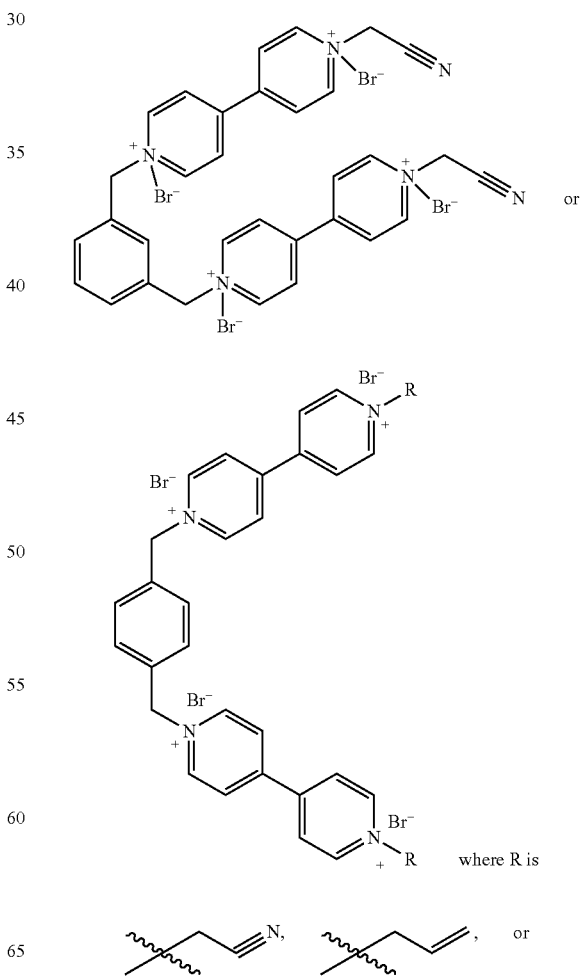

-continued

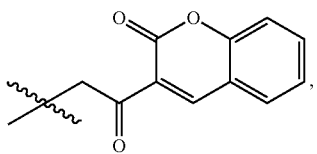

or a combination thereof.

10. The method of claim 4, where detecting the change comprises (i) comparing a color of the solution before reaction with the compound according to claim 1 to a color of the solution after reaction with the compound according to claim 1, (ii) detecting a change in absorbance of the solution at one or more wavelengths after the reaction has proceeded for the effective period of time, (iii) comparing an absorbance spectrum of the solution at a first time after combining the sample and the compound according to claim 1 to an absorbance spectrum of the solution after the reaction has proceeded for the effective period of time, (iv) detecting a change in emission of the solution at one or more wavelengths after the reaction has proceeded for the effective period of time, (v) comparing an emission spectrum of the solution at a first time after combining the sample and the compound according to claim 1 to an emission spectrum of the solution after the reaction has proceeded for the effective period of time, (vi) or any combination thereof.

11. A kit for detecting a thiol, comprising:
at least one compound according to claim 1; and
at least one buffer in which the compound according to claim 1 when combined with the thiol has an absorbance spectrum, an emission spectrum, or both that differs from an absorbance spectrum, an emission spectrum, or both when the thiol is absent.

12. The kit of claim 11, where the thiol is cysteine, homocysteine, glutathione, or a combination thereof.

13. The kit of claim 11, where the at least one compound according to claim 1 is:

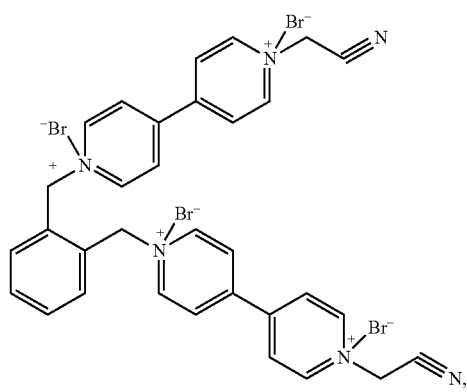

-continued

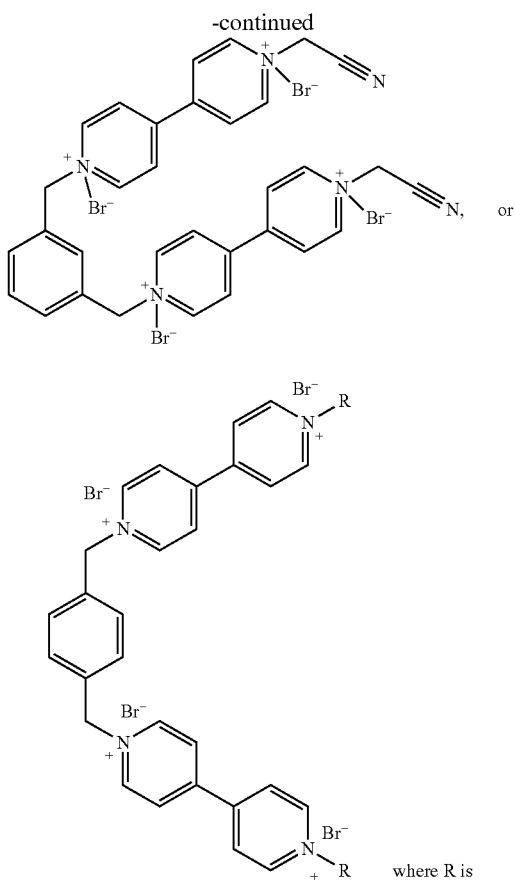

where R is

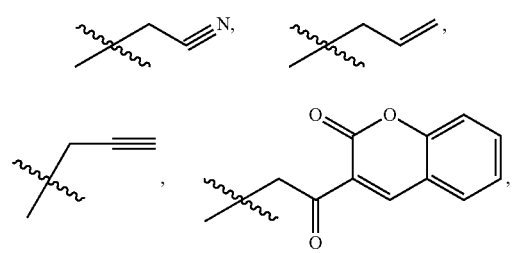

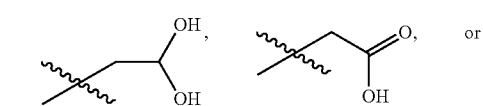

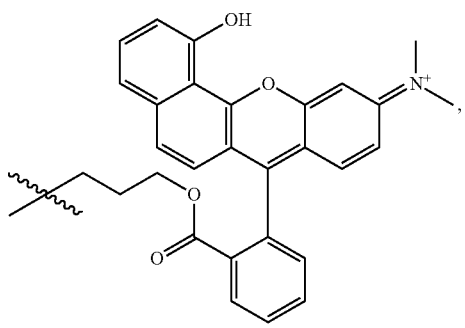

or a combination thereof.

14. The kit of claim 11, where the at least one compound according to claim 1 is:

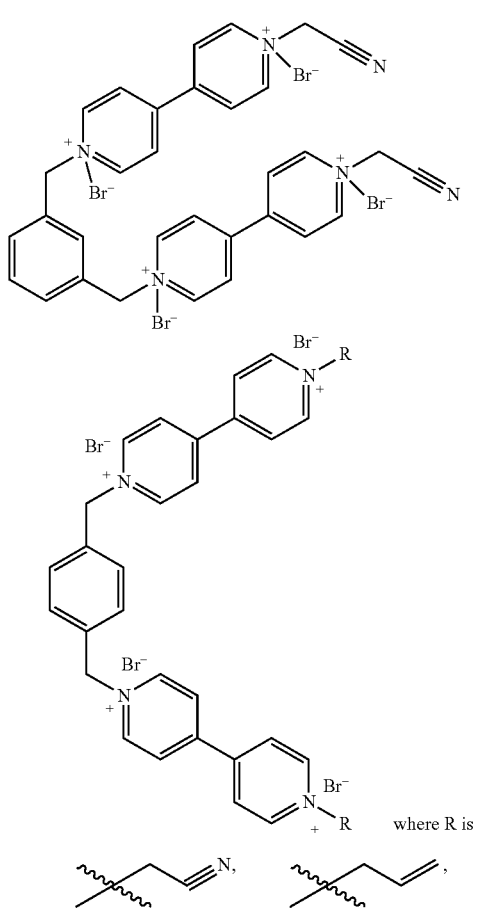

or a combination thereof.

15. The kit of claim 11, where the buffer is a HEPES (N'-2-hydroxyethylpiperazine-N'-2-ethanesulfonic acid), MOPS (3-(N-morpholino)propanesulfonic acid), phosphate, or TRIS (tris(hydroxymethyl)-aminomethane) buffer.

16. The kit of claim 11, further comprising a plurality of disposable containers in which a reaction between the compound according to claim 1 and a thiol can be performed.

17. The kit of claim 16, where an amount of the compound according to claim 1 effective to undergo a detectable change in the absorbance spectrum, the emission spectrum, or both when reacted with a thiol is premeasured into the plurality of disposable containers.

* * * * *